(12) United States Patent
Yamamoto et al.

(10) Patent No.: US 10,709,741 B2
(45) Date of Patent: Jul. 14, 2020

(54) COMPOSITION FOR PREVENTING OR TREATING INFLAMMATORY DISEASE

(71) Applicant: NATIONAL UNIVERSITY CORPORATION NAGOYA UNIVERSITY, Nagoya-shi, Aichi (JP)

(72) Inventors: Akihito Yamamoto, Nagoya (JP); Minoru Ueda, Nagoya (JP); Hidemi Goto, Nagoya (JP); Masatoshi Ishigami, Nagoya (JP); Yoshihiro Matsushita, Nagoya (JP); Yoshinori Hasegawa, Nagoya (JP); Naozumi Hashimoto, Nagoya (JP); Hirotaka Wakayama, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 582 days.

(21) Appl. No.: 14/767,331

(22) PCT Filed: Feb. 13, 2014

(86) PCT No.: PCT/JP2014/053384
§ 371 (c)(1),
(2) Date: Aug. 12, 2015

(87) PCT Pub. No.: WO2014/126176
PCT Pub. Date: Aug. 21, 2014

(65) Prior Publication Data
US 2015/0366917 A1    Dec. 24, 2015

(30) Foreign Application Priority Data
Feb. 13, 2013  (JP) .................................. 2013-025119

(51) Int. Cl.
*A61K 35/32* (2015.01)

(52) U.S. Cl.
CPC .................................. *A61K 35/32* (2013.01)

(58) Field of Classification Search
None
See application file for complete search history.

(56) References Cited

U.S. PATENT DOCUMENTS

| 2008/0226595 A1 | 9/2008 | Edinger et al. |
| 2011/0158962 A1 | 6/2011 | Ferro |
| 2013/0195991 A1* | 8/2013 | Ueda .................... A61K 35/545 424/572 |

FOREIGN PATENT DOCUMENTS

| JP | 2010-518096 A | 5/2010 |
| JP | 2011-525798 A | 9/2011 |
| WO | 2008/100498 A2 | 8/2008 |
| WO | 2009-156495 A1 | 12/2009 |
| WO | 2011/118795 A1 | 9/2011 |

OTHER PUBLICATIONS

Abdullah et al. (2014) Cell Biol. Int. 38: 582-590 (Year: 2014).*
Aquino et al. (2008) Stem Cell Rev. 4:21-26. (Year: 2008).*
Augello et al. (2007) Arthritis and Rheumatism, vol. 56, No. 4, 1175-1186 (Year: 2007).*
Ishikawa et al. (2016) Bone 83: 210-219. (Year: 2016).*
Liu et al. (2010) Arthritis Reseach and Therapy, 12: R210. (Year: 2010).*
Zhou et al. (2011) Clinical Immunology, 141, 328-337. (Year: 2011).*
Zhao et al. (2012) J. Dent. Res. 91(10): 948-854. (Year: 2012).*
Zhao et al. (2012) J. Dent. Res. 91(10): 948-954. (Year: 2012).*
Fung et al. (2012) Brain Research, 1446: 144-155 (Year: 2012).*
Iohara et al. (2008) Stem Cells 26: 2408-2418. (Year: 2008).*
Lucas et al. (2006) British J. Pharmacol. 147: S232-S240. (Year: 2006).*
Sun et al. (2005) Stroke 36: 1672-1678. (Year: 2005).*
Mari Yamagata et al., "Teisanso Kyoketsu Noshogai Model Mouse ni Taisuru Shizui Kansaibo Ishoku no Chiryo Koka", Regenerative Medicine, 2012, vol. 11, Suppl, p. 248.
Yoshihiro Matsushita et al., "Shizui Kanasaibo no Mukessei Baiyo Josei o Mochiita Nanjisei Kanshikkan no Chiryoho no Kaihatsu", Regenerative Medacine, Feb. 28, 2013 (Feb. 28, 2013), vol. 12, Suppl, p. 254.
Hirotaka Wakayama et al., "Shizui Kansaibo Yurai Mukessei Baiyo Josei o Mochiita Kyusei Haishikkan Model Mouse ni Okeru Chiryo Koka no Kento", Regenerative Medacine, Feb. 28, 2013 (Feb. 28, 2013), vol. 12, Suppl, p. 254.
Kazuhiro Kotoh et al., "Arterial Steroid injection therapy can inhibit the progression of severe acute hepatic failure toward fulminant liver failure", World Journal Gastroenterology; Nov. 7, 2006; vol. 12 (41) pp. 6678-6682.
Mas A et al., "Fulminant hepatic failure", The Lancet, Apr. 12, 1997 vol. 349. pp. 1081-1085.
Jun Li et al., "Immediate Intraportal Transplantation of Human Bone Marrow Mesenchymal Stem Cells Prevents Death From Fulminant Hepatic Failure in Pigs", Hepatology, 2012, vol. 56, No. 3, pp. 1044-1052.
Kevin R. Flaherty et al., "Steroids Idiopathic Pulmonary Fibrosis: A Prospective Assessment of Adverse Reactions, Response to Therapy, and Survival", Mar. 2001 vol. 110, pp. 278-282.
Rojas M. et al., "Bone Marrow-Derived Mesenchymal Stem Cells in repair of the Injured Lung", AMJ Respir Cell Mol Boil 2005, vol. 33 pp. 145-152.
Mar. 11, 2014 Written Opinion issued in International Patent Application No. PCT/JP2014/053384.
Aug. 13, 2014 International Preliminary Report on Patentsbility issued in International Patent Applicaton No. PCT/JP2014/053384.

(Continued)

*Primary Examiner* — Russell G Fiebig
(74) *Attorney, Agent, or Firm* — Oliff PLC

(57) ABSTRACT

A composition for preventing or treating inflammatory disease and that is effective for inflammatory disease such as fulminant hepatitis and interstitial pneumonia. For such an objective, the present uses a culture supernatant obtained by culturing dental pulp stem cells as the active ingredient of the composition for preventing or treating inflammatory disease.

6 Claims, 30 Drawing Sheets

(56) References Cited

OTHER PUBLICATIONS

Mar. 11, 2014 International Search Report issued in Interternational Patent Application No. PCT/JP2014/053384.
Nov. 7, 2017 Office Action issued in JP Application No. 2015-500294.

* cited by examiner

SHED-CM was administered on the 14th day after immunization. Decreasing of the scores was observed thereafter.

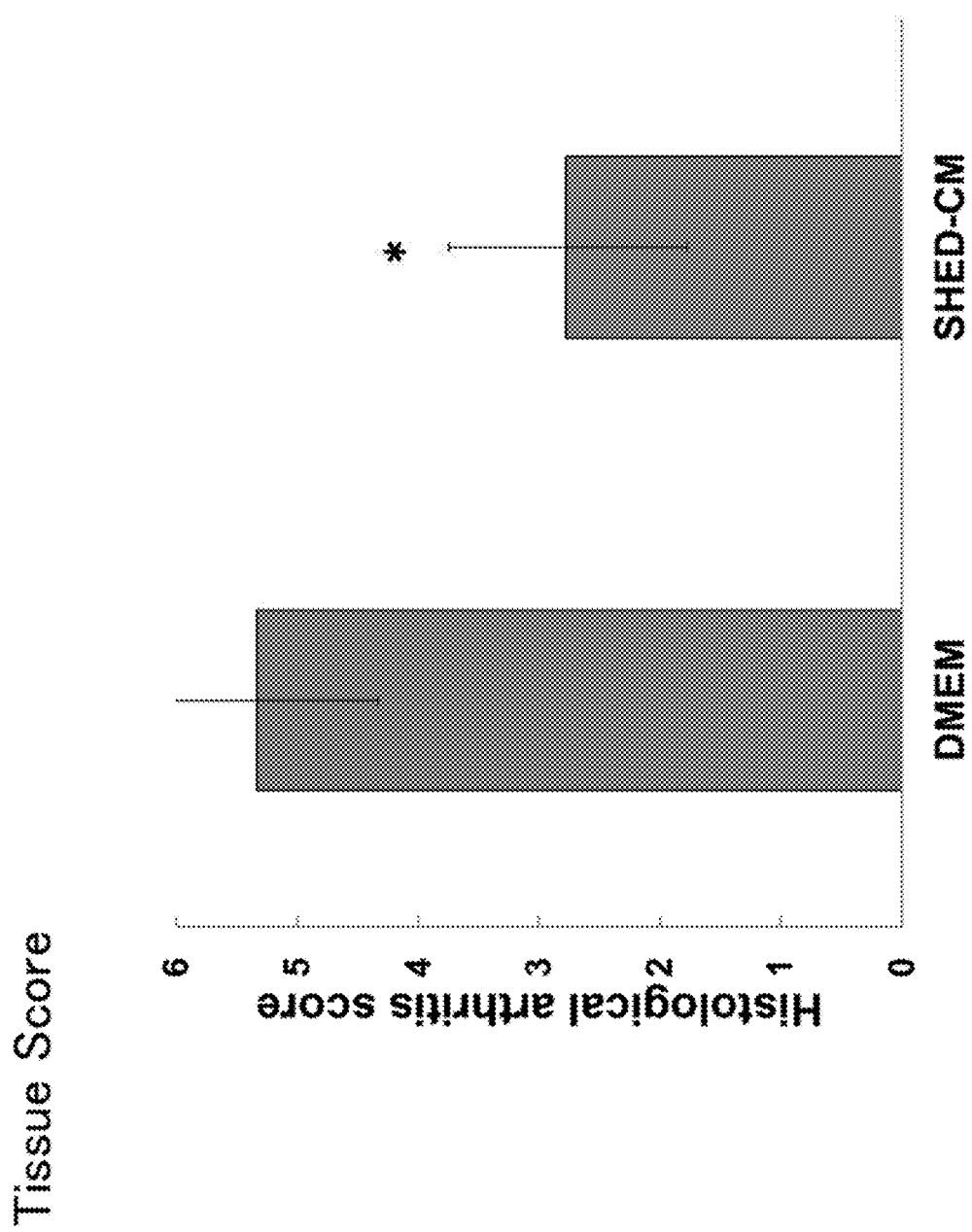

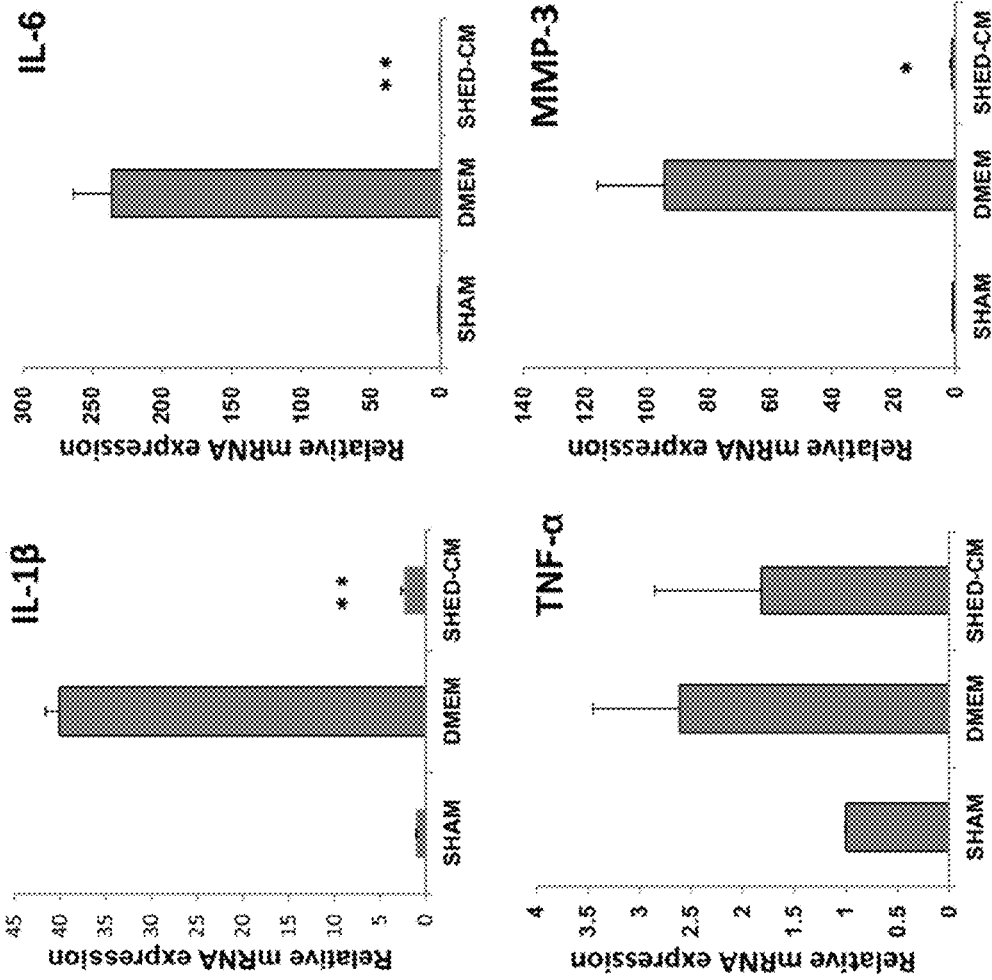

COMPOSITION FOR PREVENTING OR TREATING INFLAMMATORY DISEASE

TECHNICAL FIELD

The present Description relates to a composition for preventing or treating inflammatory disease.

BACKGROUND ART

An inflammatory reaction is a series of processes associated with the elimination of foreign matter and pathogens and the protection and repair of tissue. Excessive inflammatory reactions may cause organ damage and contribute to the occurrence of autoimmune and allergic conditions. It is thought that inflammatory disease, including acute inflammation and chronic inflammation, can be caused by infections and by allergic and autoimmune conditions, but the causes are still poorly understood.

For example, risk factors associated with one inflammatory disease, fulminant hepatitis, include infection by hepatitis viruses (especially the hepatitis B virus), drug allergies, and autoimmune factors, but the mechanism of action is still not understood. At present, liver transplantation is considered to be the most effective treatment for fulminant hepatitis. Other current treatments include steroid pulse treatment and supportive therapy using artificial liver support (Non Patent Literature 1, 2). In recent years, therapeutic effects have been reported from stem cell transplantation in a fulminant hepatitis model (Non Patent Literature 3).

Another inflammatory disease is interstitial pneumonia, which involves chronic and progressive inflammation and fibrosis of the pulmonary interstitia, although the causes are not clear. When the condition progresses to include fibrosis of inflamed tissue, it is called pulmonary fibrosis. One basic therapy is lung transplantation, but therapies using steroids and immune suppressors are common (Non Patent Literature 4). In recent years, therapeutic effects have been reported from stem cell transplantation in a pulmonary fibrosis model (Non Patent Literature 5).

A composition containing culture supernatant of dental pulp stem cells or other stem cells has been described as effective for treating injuries (Patent Literature 1).

CITATION LIST

Patent Literature

Patent Literature 1: WO 2011/118795

Non Patent Literature

Non Patent Literature 1: Kazuhiro K et al; World J Gastroenterol; 2006
Non Patent Literature 2: Mas A et al; The Lancet; 1997
Non Patent Literature 3: Jun L et al; Hepatology; 2012
Non Patent Literature 4: Kevin R. Flaherty et al; Am J Med; 2001
Non Patent Literature 5: Rojas M et al; Am J Respir Cell Mol Biol; 2005

SUMMARY

However, there is a shortage of donors for liver and lung transplantation. There have also been few cases of clinical improvement from using steroid pulse therapy and artificial liver support for fulminant hepatitis. Moreover, steroids and the like often have various side effects when used for interstitial pneumonia. In stem cell transplantation, there is a risk that the transplanted stem cells will become cancerous.

Although a composition containing culture supernatant of dental stem cells or other stem cells may be effective for tissue injury in cases of gingivitis, spinal cord injury and the like, it cannot be generally assumed that it will be effective in cases of inflammatory disease such as fulminant hepatitis and interstitial pneumonia.

The present Description provides a composition for preventing or treating inflammatory disease, effective for inflammatory diseases such as fulminant hepatitis and interstitial pneumonia.

Solution to Technical Problem

After investigating therapies for fulminant hepatitis and pulmonary fibrosis, which are intractable inflammatory diseases, the inventors discovered that a culture supernatant of dental pulp stem cells is surprisingly effective. The present Description provides the following means based on these findings.

(1) A composition for preventing or treating inflammatory disease, containing a culture supernatant obtained by culturing dental pulp stem cells.

(2) The composition according to (1), containing no serum.

(3) The composition according to (1) or (2), not containing the dental pulp stem cells.

(4) The composition according to any one of (1) to (3), wherein the inflammatory disease is selected from the group consisting of fulminant hepatitis, acute hepatitis, chronic hepatitis, hepatic cirrhosis, acute interstitial pneumonia, chronic interstitial pneumonia and pulmonary fibrosis.

(5) The composition according to any one of (1) to (3), wherein the inflammatory disease is selected from chronic hepatitis and hepatic cirrhosis.

(6) The composition according to any one of (1) to (3), wherein the inflammatory disease is an inflammatory autoimmune disease.

(7) The composition according to (6), wherein the inflammatory autoimmune disease is selected from the group consisting of multiple sclerosis, systemic lupus erythematosus and rheumatoid arthritis.

(8) The composition according to any one of (1) to (3), wherein the inflammatory disease is an ischemic heart disease.

(9) The composition according to (8), wherein the ischemic heart disease is myocardial infarction.

(10) A method for manufacturing a composition for prevention or treatment according to any one of (1) to (9), wherein adherent cells are selected from dental pulp cells, the adherent cells are cultured, and a culture supernatant is collected.

(11) A method for preventing or treating inflammatory disease, comprising the administration of the composition according to any one of (1) to (9) to an individual suffering from inflammatory disease in a dose effective for preventing or treating the inflammatory disease.

(12) The method according to (11), wherein the composition is administered by an administration method selected from the group consisting of intravenous administration, intra-arterial administration, intraportal administration, intracutaneous administration, subcutaneous administration, intramuscular administration, intraperitoneal administration and intranasal administration.

(13) The method according to (11) or (12), wherein the inflammatory disease is selected from the group consisting of fulminant hepatitis, acute hepatitis, chronic hepatitis, hepatic cirrhosis, acute interstitial pneumonia, chronic interstitial pneumonia and pulmonary fibrosis.

(14) The method according to (11) or (12), wherein the inflammatory disease is selected from chronic hepatitis and hepatic cirrhosis.

(15) The method according to (11) or (12), wherein the inflammatory disease is an inflammatory autoimmune disease.

(16) The method according to (15), wherein the inflammatory autoimmune disease is selected from the group consisting of multiple sclerosis, systemic lupus erythematosus and rheumatoid arthritis.

(17) The method according to (11) or (12), wherein the inflammatory disease is an ischemic heart disease.

(18) The method according to (17), wherein the ischemic heart disease is myocardial infarction.

BRIEF DESCRIPTION OF DRAWINGS

FIG. 29 shows the results of ankle tissue analysis following SHED-CM administration in arthritis model mice.

FIG. 30 shows the results of gene expression analysis in the four limbs following SHED-CM administration in arthritis model mice.

DESCRIPTION OF EMBODIMENTS

Figure 1:
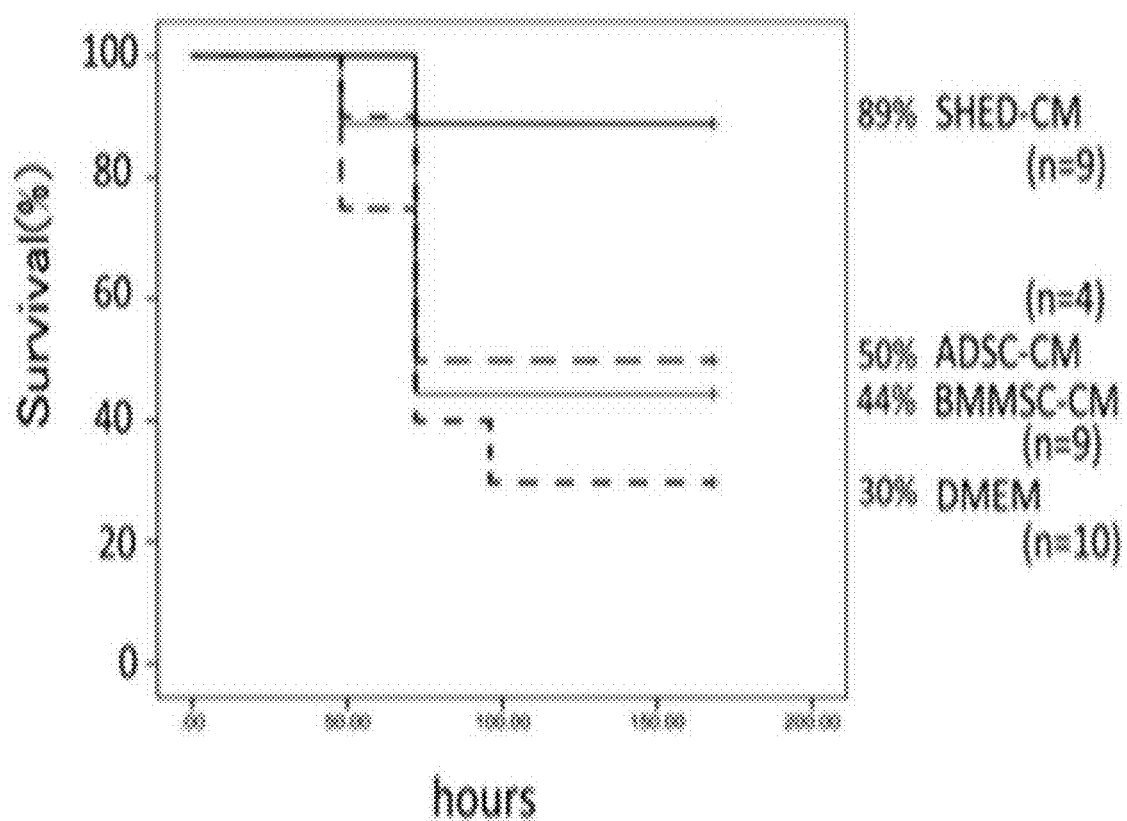
FIG. 1 shows survival rates for fulminant hepatitis model rats.

Composition for Preventing or Treating Inflammatory Disease

The present Description relates to a composition for preventing or treating inflammatory disease. This composition may contain culture supernatant obtained by culturing dental pulp stem cells. This culture supernatant contains various cytokines. According to Patent Literature 1, because this culture supernatant contains such cytokines, it can cause cells to proliferate at an injury site, resulting in recovery of the tissue of the injury site. The inventors discovered a hitherto unknown property of this culture supernatant, namely, the therapeutic effects of the culture supernatant when administered to treat fulminant hepatitis, pulmonary fibrosis and other intractable inflammatory diseases. Although this culture supernatant contains a variety of cytokines, even the inventors, as persons skilled in the art, had not expected that it would be effective against inflammatory disease of unknown cause.

With this composition, it is possible to effectively prevent or treat inflammatory disease while avoiding the problems of organ transplantation (donor shortage), conventional hormone therapy (side effects and poor effectiveness) and stem cell transplantation.

Although this does not restrict the disclosures of the present Description, the composition can induce immunocompetent cells (macrophages) to differentiate or be converted into the tissue-repairing type. Thus, delivering the composition to an inflammatory reaction site is a way of actively applying tissue-repairing macrophages and activating tissue repair at the inflammatory reaction site.

In the present Description, "inflammation" means a mechanism in mammals that is induced by the presence of foreign matter or tissue injury due to some cause, and that acts to protect the body. An "inflammatory reaction" is a series of processes that occur in inflammation. The term "inflammatory reaction" may encompass tissue damage induced by inflammation. An "inflammatory disease" is a disease, disorder or symptoms characterized by inflammation of bodily tissue or the presence of inflammatory elements. These include local inflammatory reactions and systemic inflammatory reactions.

The composition may contain a culture supernatant obtained by culturing somatic stem cells from dental pulp, or in other words dental pulp stem cells.

(Dental Pulp Stem Cells)

The dental pulp stem cells are not particularly limited as long as they are stem cells obtained from dental pulp and derived from dental pulp. They may be permanent tooth dental pulp stem cells or deciduous tooth dental pulp stem cells, but from the standpoint of cell proliferative potential, dental pulp stem cells from exfoliated deciduous teeth are preferred. Considering the individual in which the composition is to be used, dental pulp stem cells from the same species (human in the case of a human subject) are preferred in order to suppress or avoid rejection reactions, and more preferably autologous dental pulp stem cells are used.

The dental pulp stem cells may be selected by selecting adherent cells from among dental pulp cells. Culture supernatant obtained by culturing the adherent cells from among dental pulp cells collected from exfoliated deciduous teeth or permanent teeth, or passage cells of these, can be used as a "culture supernatant of dental pulp stem cells". For example, the methods given below, which are described in Japanese Patent Application Publication No. 2011-219432 and the like, can be applied appropriately.

Immortalized cells of dental pulp stem cells may also be provided. Normally 1 or 2 or more, or preferably 3 or more, or more preferably 4 or more genes are introduced when immortalizing dental pulp stem cells. For this reason, the immortalized cells no longer have properties equivalent to those of the original dental pulp stem cells. It is well known to those skilled in the art that the products and secretions and amounts of these differ between original cells and their immortalized cells. Thus, the original dental pulp stem cells have different products from the immortalized cells derived from these dental pulp stem cells, and the condition and composition of the secretions is different. Therefore, culture supernatant of dental pulp stem cells and culture supernatant of immortalized cells derived from dental pulp stem cells differ greatly in terms of their compositions, or in other words in the types and proportions of their components. As a result, the action and therapeutic effects of the culture supernatant against inflammatory disease is different for dental pulp stem cells and immortalized cells derived from dental pulp stem cells.

(1) Collection of Dental Pulp

Naturally exfoliated deciduous teeth (or extracted deciduous teeth, or permanent teeth) were disinfected with chlorhexidine or Isodine solution, the crown parts were split off, and the dental pulp tissue was collected with a dental reamer.

(2) Enzyme Treatment

The collected dental pulp tissue is suspended in basic medium (Dulbecco's Modified Eagle's Medium containing 10% bovine serum/antibiotic), and treated for one hour at 37° C. with 2 mg/ml collagenase and dispase. After enzyme treatment the dental pulp cells are collected by 5 minutes of centrifugation (5000 rpm). Cell selection with a cell strainer is avoided in principle because it reduces the recovery efficiency of neural stem cell fraction of SHED and DPSC cells.

(3) Cell Culture (Selection of Adherent Cells)

The cells are re-suspended in 4 cc of basic medium, and seeded on an adherent cell culture dish 6 cm in diameter. They are cultured for 3 days in an incubator adjusted to 5% $CO_2$, 37° C., after which the colony-forming adherent cells are treated for 5 minutes at 37° C. with 0.05% trypsin/EDTA. The dental pulp cells are detached from the dish, seeded on an adherent cell culture dish 10 cm in diameter, and expansion cultured. For example, once cells have become sub-confluent (occupying about 70% of the surface of the culture container) or confluent as observed with the naked eye, they are detached from the culture container and collected, and then seeded again in a culture container filled with culture liquid. Sub-culture may also be repeated. For example, cells may be sub-cultured 1 to 8 times until the necessary number of cells (for example about $1\times10^7$/ml) is obtained. Detachment of the cells from the culture container may be accomplished by an ordinary method such as trypsin treatment. After this culture, the cells may also be collected and stored (storage conditions −198° C. for example).

(Alternative Method)

The cells are re-suspended in 4 cc of basic medium, and seeded on an adherent cell culture dish 6 cm in diameter. Culture liquid (for example, DMEM (Dulbecco's Modified Eagle's Medium) containing 10% FCS) is added, and the cells are cultured for about 2 weeks in an incubator adjusted to 5% $CO_2$, 37° C. The culture liquid is removed, and the cells are washed once or multiple times with PBS or the like. In place of this operation (culture liquid removal and cell washing), it is also possible to collect colony-forming adherent cells (dental pulp stem cells). In this case, they are treated for 5 minutes at 37° C. with 0.05% trypsin/EDTA for example, and collected by detaching them from the dish.

(4) Cell Collection

Next, the cells are collected. The cells are first detached from the culture container by trypsin treatment or the like, after which they can be collected by centrifugation. The dental pulp stem cells thus collected are used to prepare the composition of the present invention.

(Culture Supernatant of Dental Pulp Stem Cells)

A culture supernatant of dental pulp stem cells is a supernatant of culture liquid obtained by culturing dental pulp stem cells. This means that it contains effectively no cell components (dental pulp stem cells or dental pulp cells). The composition typically contains no dental pulp stem cells or dental pulp cells, and is composed solely of culture supernatant of dental pulp stem cells. The cultured dental pulp stem cells are removed after culture by separating and removing the cell components. Separation of the cell components from the culture liquid can be accomplished by methods well known to those skilled in the art. It is also possible to use a culture supernatant obtained by treating the culture liquid in various ways (for example, centrifugation, concentration, solvent substitution, dialysis, freezing, drying, freeze-drying, dilution, desalting, storage, etc.) as necessary.

Basic medium or basic medium with serum and the like added thereto can be used for culturing the dental pulp stem cells. In addition to DMEM, Iscove's modified Dulbecco's Medium (IMDM) (Gibco), HamF12 medium (Sigma, GIBCO, etc.), RPMI1640 medium or the like may be used as the basic medium. Two or more kinds of basic medium may also be used together. One example of a mixed medium is one in which equal amounts of IMDM and HamF12 are mixed together (available commercially as IMDM/HamF12 (Gibco) for example). Examples of components that may be added to the medium include serum (fetal bovine serum, human serum, ovine serum, etc.), serum replacements (Knockout Serum Replacement (KSR), etc.), bovine serum albumin (BSA), antibiotics, various vitamins and various minerals.

The composition preferably does not contain serum. Safety is increased if no serum is included. For example, a culture supernatant containing no serum can be prepared by culturing dental pulp stem cells in medium containing no serum (serum-free medium). Regardless of whether sub-culture is performed once or multiple times, a culture supernatant containing no serum can be obtained if either the final sub-culture or the final few sub-cultures are performed in serum-free medium. Alternatively, a culture supernatant containing no serum can also be obtained by removing the serum from the collected supernatant by dialysis or solvent replacement using a column or the like.

(Obtaining Culture Supernatant)

Conditions commonly used for stem cells can be used as is or with suitable alterations for culturing the dental pulp stem cells. A dental pulp stem cell culture supernatant can be manufactured appropriately by a person skilled in the art. For example, a culture supernatant can be obtained by operations such as the following.

First, as explained previously, adherent cells selected from dental pulp (dental pulp stem cells) are cultured in the medium described above. For example, the cells are seeded on an adherent cell culture dish, and cultured in an incubator adjusted to 5% $CO_2$, 37° C. Sub-culture is performed as necessary. For example, once cells have become sub-confluent (occupying about 70% of the surface of the culture container) or confluent as observed with the naked eye, they are detached from the culture container and collected, and then seeded again in a culture container filled with culture liquid. Sub-culture may also be repeated. For example, cells may be sub-cultured 1 to 8 times until the necessary number of cells (for example about $1\times10^7$/ml) is obtained. Detachment of the cells from the culture container may be accomplished by an ordinary method such as trypsin treatment. After this culture, the cells may also be collected and stored (storage conditions −198° C. for example).

Next, a culture supernatant of the selected and cultured dental pulp stem cells is collected. For example, the culture liquid can be suctioned and collected with a dropper or pipette. The collected culture supernatant may be used as the active ingredient of the composition of the present invention, either as is or after being subjected to one or more treatments. Examples of treatments here include centrifugation, concentration, solvent substitution, dialysis, freezing, drying, freeze-drying, dilution, desalting and storage (for example at 4° C. or −80° C.).

The culture supernatant may also be concentrated as necessary. That is, the supernatant may be included as a concentrate. The concentration method may be selected appropriately by a person skilled in the art from known methods. For example, a concentrate of the culture supernatant may be obtained by spin column concentration or ethanol precipitation concentration. This culture supernatant may also be subjected to freeze drying. That is, the culture supernatant may be a freeze-dried product.

(Components and Form of Composition)

The composition is a culture supernatant of dental pulp stem cells, and may contain low-molecular-weight organic compounds in addition to proteins and other high-molecular-weight compounds secreted in the culture by the dental pulp stem cells. Because it is a culture supernatant, the composition may also contain components derived from the medium.

The composition may take a liquid (liquid, gel, etc.) or solid (powder, fine particles, granules, etc.) form. The composition may also be formulated in various known ways according to the type of disease, the characteristics of the individual having the disease, and the administration method and dosage. Examples include tablets, powders, grains, granules, fine particles, capsules, solid injections to be dissolved at the time of use, suppositories and other solid preparations, liquid injections (intravenous/intramuscular), impregnating agents, drops and other liquid preparations, and eye drops, sprays, lotions, creams, patches and other topical preparations and the like. It may also be supported on an indwelling medical device or the like. In addition, the composition may contain known pharmacologically acceptable salts. A person skilled in the art can formulate it appropriately.

The composition can contain other pharmaceutically acceptable components suited to the type of disease and formulation. Other pharmaceutically acceptable components (for example, carriers, excipients, disintegrants, buffers, emulsifiers, suspension agents, soothing agents, stabilizers, preservatives, antiseptic agents, physiological saline, etc.) may also be included. Excipients that can be used include lactose, starch, sorbitol, D-mannitol, sugar and the like. Disintegrants that can be used include starch, carboxymethyl cellulose, calcium carbonate and the like. Buffers that can be used include phosphate salts, citrate salts, acetate salts and the like. Emulsifiers that can be used include gum arabic, sodium alginate, tragacanth and the like. Suspension agents that can be used include glycerin monostearate, aluminum monostearate, methylcellulose, carboxymethyl cellulose, hydroxymethyl cellulose, sodium lauryl sulfate and the like. Soothing agents that can be used include benzyl alcohol, chlorobutanol, sorbitol and the like. Stabilizers that can be used include propylene glycol, ascorbic acid and the like. Preservatives that can be used include phenol, benzalkonium chloride, benzyl alcohol, chlorobutanol, methyl paraben and the like. Antiseptic agents that can be used include benzalkonium chloride, parahydroxybenzoic acid, chlorobutanol and the like. Antibiotics, pH adjusters, growth factors (for example, epithelial cell growth factor (EGF), nerve growth factor (NGF) and brain-derived neurotrophic factor (BDNF)) and the like may also be included.

The composition may be used for prevention or treatment of inflammatory disease. This includes a wide range of inflammatory diseases, with no particular limitations. Examples of inflammatory diseases include Sjogren's syndrome, dry eye, skin wound healing, myocardial infarction, immune rejection associated with bone marrow transplantation, arthritis, rheumatoid arthritis, osteoarthritis, bone disease associated with increased bone absorption and other chronic inflammatory joint diseases; ileitis, ulcerative colitis, Barrett's syndrome, Crohn's disease and other inflammatory bowel disorders; asthma, acute and chronic interstitial pneumonia, pulmonary fibrosis, adult respiratory distress syndrome, chronic obstructive airway disorder and other inflammatory lung diseases; trachoma, onchocerciasis, uveitis, sympathetic ophthalmitis, endophthalmitis and other inflammatory eye diseases; gingivitis, periodontitis and other chronic inflammatory periodontal diseases; tuberculosis, Hansen's disease, complications of uremia, glomerular nephritis, nephrosis and other inflammatory kidney diseases;

sclerodermatitis, psoriasis, eczema and other inflammatory skin diseases; immune complex vasculitis, systemic lupus and erythema, multiple sclerosis, systemic lupus erythematosus (SLE) and other inflammatory autoimmune diseases; myocarditis, myocardial infarction and other ischemic heart diseases, hypercholesterolemia, atherosclerosis and other inflammatory heart diseases; and preeclampsia, chronic liver failure, chronic hepatitis, hepatic cirrhosis, acute hepatitis, fulminant hepatitis, brain, cancer and various other diseases involving serious inflammation. Other examples are systemic inflammations including gram-positive or gram-negative bacterial shock, hemorrhagic or anaphylactic shock, and shock induced by chemotherapy methods that respond to proinflammatory cytokines (for example, proinflammatory cytokine-associated shock). Such shock may be induced for example by chemotherapy drugs used in cancer chemotherapy. Other examples include skin transplant rejection reactions and other transplant rejection reactions. Of these, the composition may be applied favorably to acute and subacute diseases and conditions. Examples include acute hepatitis and fulminant hepatitis. It can also be applied favorably to chronic interstitial pneumonia, acute interstitial pneumonia and pulmonary fibrosis. It can also be applied favorably to chronic hepatitis, hepatic cirrhosis and other chronic liver diseases. It can also be applied favorably to myocardial infarction and other ischemic heart diseases. It can also be applied favorably to rheumatoid arthritis, multiple sclerosis, system lupus erythematosus and other inflammatory autoimmune disorders.

The route of administration of the composition is not particularly limited. Various known administration forms may be adopted according to the target site and the disease to be treated. For example, non-oral administration may be systemic or local. More specifically, administration may be by infusion, embrocation or spraying on the site of inflammation. Other examples include intravenous administration, intra-arterial administration, intraportal administration, intracutaneous administration, subcutaneous administration, intramuscular administration, intraperitoneal administration, intranasal administration and intraoral administration.

The dosage of the composition is not particularly limited, and may be set after considering the age, weight and condition of the subject and the like. For example, an administration schedule might be once to several times a day, once every two days or once every three days. When preparing the administration schedule, the gender, age, body weight, condition and the like of the subject (recipient) may be considered.

The subjects to which this composition may be given include humans and other mammals (pets, livestock, experimental animals, etc.). Examples include humans as well as dogs, cats, rabbits, mice, cows, pigs, goats, sheep, horses, monkeys, guinea pigs, rats and mice.

(Method for Preventing or Treating Inflammatory Disease)

The method for prevention or treatment disclosed in this Description may comprise the administration of the composition to an individual suffering from inflammatory disease in a dose effective for preventing or treating the inflammatory disease. With this treatment method, it is possible to at once resolve the problems of prior art and prevent or treat inflammatory disease. The embodiments described above for the composition, administration method and the like may be applied to this method.

(Method for Screening Factors or Combinations of Factors Effective for Preventing or Treating Inflammatory Disease)

The disclosures of this Description provide a method for screening factors or combinations of factors effective for preventing or treating inflammatory disease, provided with a step of supplying one or two or more components contained in a culture supernatant obtained by culturing dental pulp stem cells to an evaluation system for inflammatory disease, and evaluating their effects on inflammatory disease.

With this screening method, it is possible to find out which components contained in a culture supernatant of dental pulp stem cells are effective against various inflammatory diseases, and to obtain a composition for prevention or treatment that contains the specified dental pulp stem cell culture supernatant components as active ingredients, or in other words that mainly contains only the specified culture supernatant components as active ingredients. Because such a composition is not derived from a culture supernatant of dental pulp stem cells, moreover, it is possible to obtain an effective composition for prevention or treatment by combining specific components that have been obtained commercially and/or by purification or the like.

Regarding the evaluation system for inflammatory disease used in this screening method, systems for various inflammatory diseases are well known. For example, model mice can be used for fulminant hepatitis, pulmonary fibrosis, hepatic cirrhosis, ischemic heart disease, multiple sclerosis, SLE, arthritis and various other inflammatory diseases, and evaluation systems using associated cells can also be selected and used appropriately. A person skilled in the art can select such evaluation systems as necessary, or they may be selected appropriately with reference to the examples and the like of the present Description.

The components shown below (which are listed by their protein, gene or substance names or common names or the like) are contained in culture supernatant of dental pulp stem cells. One or two or more or three or more selected from these components may be combined appropriately and applied to screening effective factors for inflammatory disease.

| | |
|---|---|
| GRO | Platelet factor 4 |
| MMP-10 | IGFBP-6 |
| Follistatin | Growth Hormon |
| LYVE-1 | Trappin-2 |
| TACE | GDF-15 |
| NRG1 | IL-29 |
| MMP-7 | beta IG-H3 |
| Furin | IL-5R alpha |
| Angiogenin | Siglec-9 |
| RANK | BCAM |
| Galectin-7 | HGF |
| NrCAM | Lymphotactin |
| Axl | VEGF-C |
| MMP-3 | Osteoprotegerin |
| TSLP | TIMP-2 |
| Ferritin | MIF |
| XEDAR | ALCAM |
| FLRG | TIM-1 |
| CD40 | CCL-28 |
| DKK-3 | CD30 |
| Resistin | MCP-1 |
| sTNT R1 | Thrombopoietin |
| Nidogen-1 | IL-6 R |
| TRAIL R2 | SAA |
| IL-22 | LIMPII |
| MMP-2 | MMP-8 |
| Marapsin | Erythropoietin R |

-continued

| | |
|---|---|
| NCAM-1 | PlGF |
| MICA | sgp130 |
| Fcr RIIB/C | TIMP-1 |
| Insulin | VEGF |
| SCF | IL-28A |
| Osteopontin | TRAIL R3 |
| LAP | |

[1]

EXAMPLES

The present invention is explained in detail below using examples, but the following examples do not limit the present invention. In the examples below, percentages are all mass percentages.

Example 1

(Preparation of Dental Pulp Stem Cell Culture Supernatant (SHED-CM) from Human Exfoliated Deciduous Teeth)

Dental pulp stem cells from human exfoliated deciduous teeth were cultured in a 10 cm dish in DMEM (SIGMA ALORICH CO. USA)+10% FBS (SIGMA ALORICH CO USA)+1% Penicillin Streptomycin (Life Technologies Japan Ltd) to 80 to 90% confluence. These were washed twice with PBS, transferred to serum-free culture liquid (DMEM), and cultured for 48 hours. The supernatant was collected and centrifuged for 4 to 5 minutes at 1500 rpm and 5 minutes at 3000 rpm, and the resulting supernatant was used in the following examples as dental pulp stem cell culture supernatant.

Example 2

Figure 2:
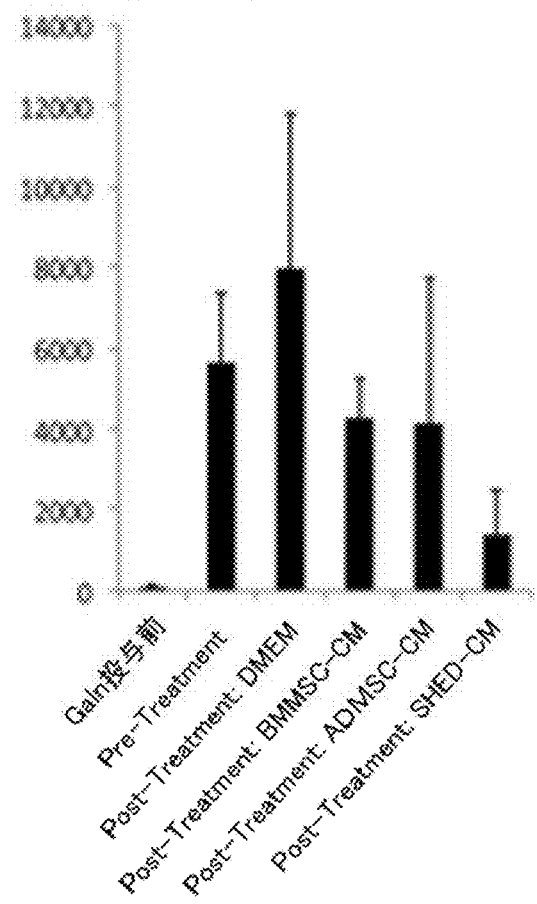
FIG. 2 shows the results of an evaluation of liver damage by blood testing in fulminant hepatitis model rats.
Figure 2:
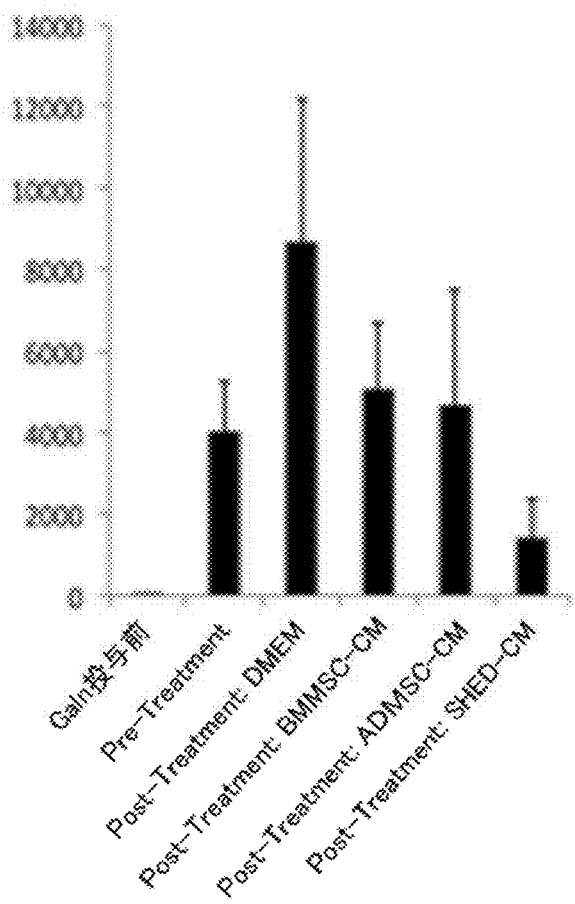

(Analysis of Therapeutic Usefulness of Dental Pulp Stem Cells in Fulminant Hepatitis Model)
(1) Preparation of Fulminant Hepatitis Model Rats A D-glactosamine solution for inducing severe liver damage was prepared by dissolving in PBS/NaOH solution. This solution was administered intraperitoneally to Sprague-Dawley rats (200 to 250 g) to 1.2 g of D-galactosamine per kg of rat weight. 24 hours after administration blood was taken, and AST and ALT were measured to confirm induction of severe liver damage (fulminant hepatitis). Next, 1 ml of the (serum-free) dental pulp stem cell culture supernatant (SHED-CM) prepared in Example 1 was administered through the jugular veins, and clinical improvement was tested. 1 ml of serum-free culture supernatants of adipose stem cells and myeloid stem cells were also injected through the jugular veins as comparative examples. As a control, 1 ml of DMEM was injected through the jugular veins of rats 24 hours after occurrence of fulminant hepatitis (24 hours after galatosamine administration).
(2) Determination of 1-week Survival Rates, Evaluation of Liver Damage by Blood Testing FIG. 1 and FIG. 2 show 1-week survival rates and the results of an evaluation of liver damage by blood testing, respectively. A D-galactosamine solution for inducing severe liver damage was administered intraperitoneally at a rate of 1.2 g/kg to Sprague-Dawley rats (200 to 250 g). As shown in FIG. 1, the 1-week survival rate was reduced to 30% or less in the DMEM administration group (n=10). By contrast, there was dramatic clinical improvement in the group receiving the dental pulp stem cell serum-free culture supernatant, with a 1-week survival rate of 90%. In the adipose stem cell serum-free culture supernatant administration group and/or myeloid stem cell serum-free culture supernatant administration group, not much clinical improvement was obtained (50% and 44%, respectively).

Moreover, as shown in FIG. 2, the blood AST and ALT values were about 8000 U/L and about 8000 U/L in the DMEM administration group, but about 1000 U/L each in the dental pulp stem cell serum-free culture supernatant administration group. In the adipose stem cell serum-free culture supernatant administration group and myeloid stem cell serum-free culture supernatant administration group, both values were about 4000 U/L and/or about 5000 U/L. These results support the results for survival rates shown in FIG. 1. The benchmarks for cell damage are AST=6000 U/L, ALT=4000 U/L.
(3) Pathological Analysis in Fulminant Hepatitis Model Widespread liver cell death and impaired liver cell regeneration are observed in the livers of fulminant hepatitis patients. Pathology was evaluated in these model rats by analyzing these factors. That is, liver cell death was evaluated by HE staining and TUNEL staining, while liver cell regeneration was evaluated by Ki-67 staining. TUNEL stain results are shown in FIG. 3.

Figure 3:
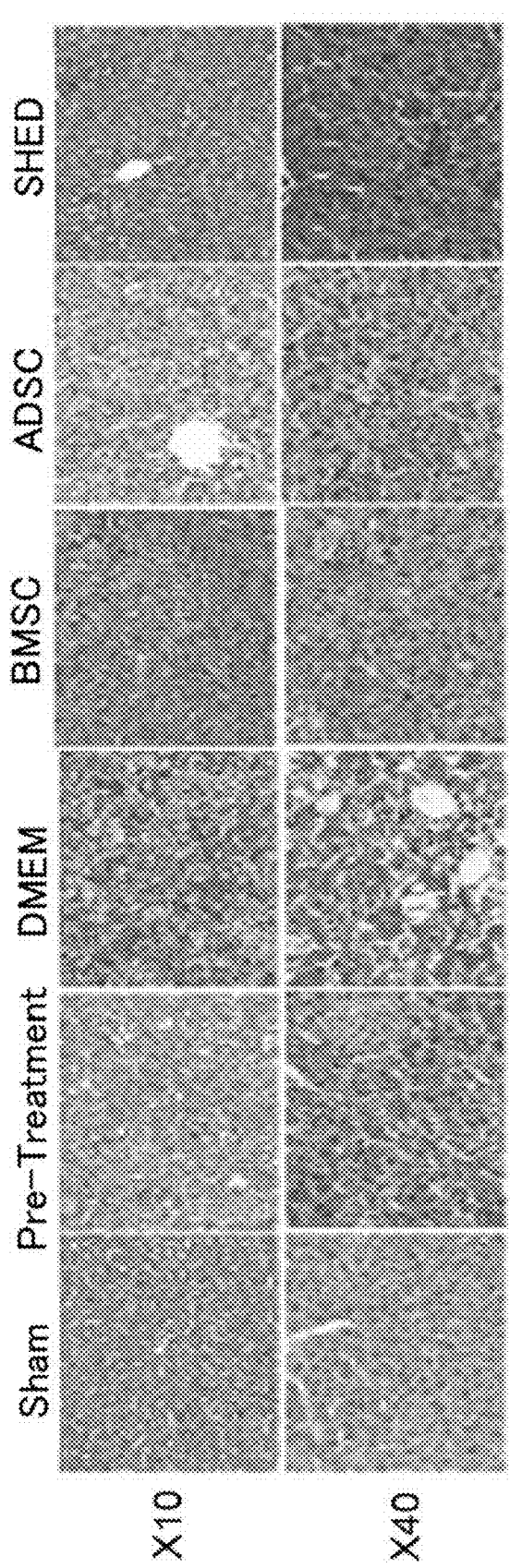
FIG. 3 shows the results (HE stain) of a pathological analysis in fulminant hepatitis model rats.
Figure 4:
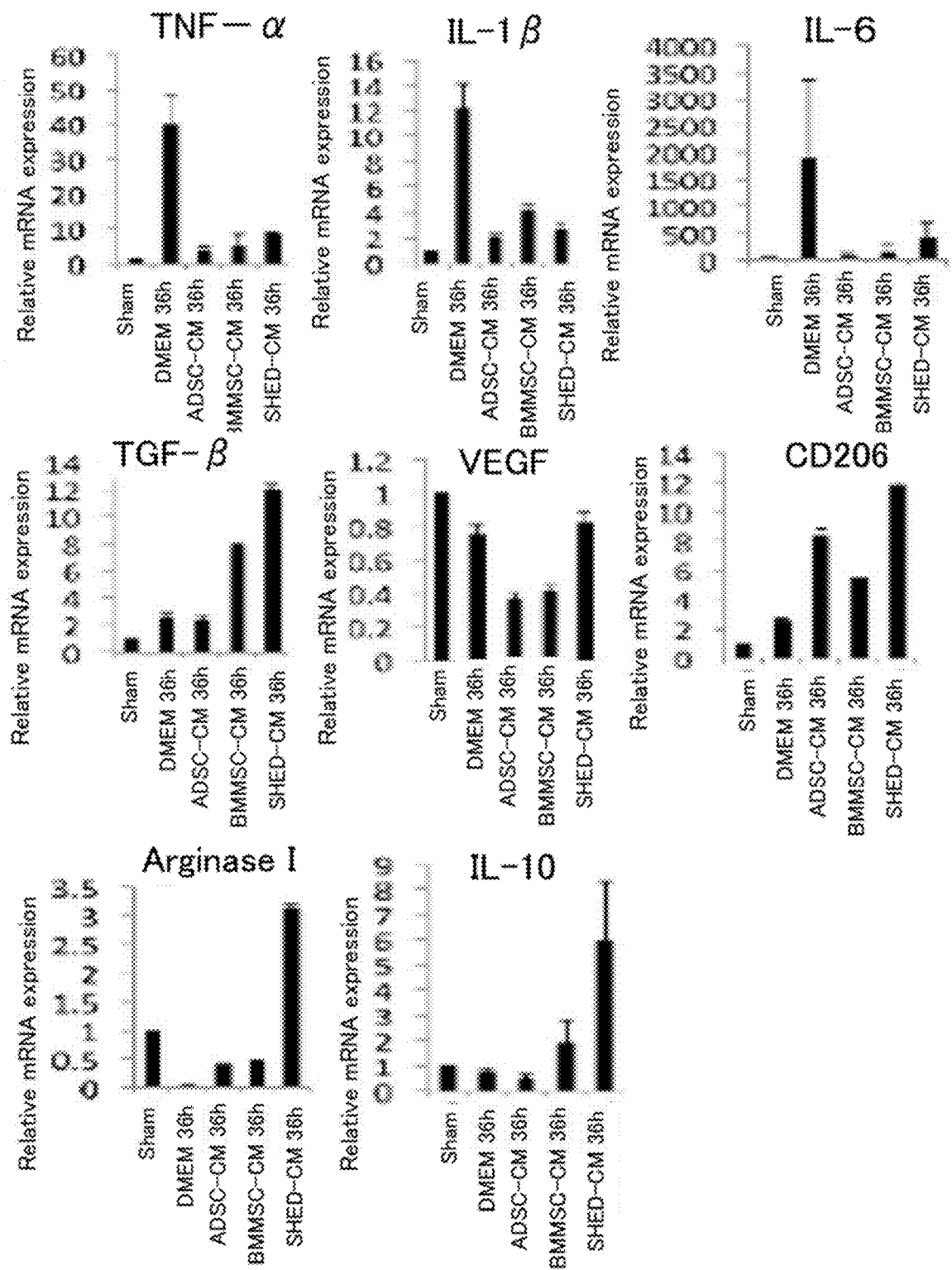
FIG. 4 shows the results of an analysis of gene expression of proinflammatory cytokines (TNF-α, IL-1β, IL-6), a dead cell sensor called mannose receptor CD206, and anti-inflammatory cytokines (IL-10, TGF-b) in fulminant hepatitis model rats.

As shown in FIG. 3, severe vacuolar degeneration and many Tunel-positive cells (20% of total liver cells) were detected in the DMEM administration group. A tissue image taken 12 hours after administration of the serum-free culture supernatant (CM) of dental pulp stem cells showed normal liver tissue. The number of Tunel-positive cells was also much less. These results support the results shown in FIG. 1 and FIG. 2.
(4) Gene Analysis in Fulminant Hepatitis Model In severe inflammatory reactions, inflammatory tissue-destroying M1 macrophages and anti-inflammatory tissue repairing M2 macrophages play an important role in hepatic tissue injury. M1 macrophages promote genetic expression of proinflammatory cytokines (TNF-α, IL-1β, IL-6), and also promote active oxygen production (iNOS). M2 macrophages express large quantities of dead cell sensors: mannose receptor CD206, the free radical synthesis inhibiting factor Arginase, and anti-inflammatory cytokines (IL-10, TGF-β). In the model rats in this case, the produced amounts of these factors were analyzed by quantitative RT-PCR to evaluate pathology. The results are shown in FIG. 4. The primers used in quantitative RT-PCR are shown in Table 1.

TABLE 2

| Origin | Primer | Sequence (forward 5'-3') | Sequence (reverse 5'-3') |
|---|---|---|---|
| rat | GAPDH | AACTTTGGCATCGTGGAAGG | CGGATACATTGGGGGTAGGA |
| rat | IL-6 | TTGCCTTCTTGGGACTGATG | ACTGGTCTGTTGTGGGTGGT |
| rat | IL-1β | CAGGATGAGGACCCAAGCAC | TCAGACAGCACGAGGCATTT |

TABLE 2-continued

| Origin | Primer | Sequence (forward 5'-3') | Sequence (reverse 5'-3') |
|---|---|---|---|
| rat | TNF-α | CTCGAGTGACAAGCCCGTAG | CCTTGAAGAGAACCTGGGAGTAG |
| rat | iNOS | GGCAGGATGAGAAGCTGAGG | CCGCATTAGCACAGAAGCAA |
| rat | IL-10 | GCCTGCTCTTACTGGCTGGA | TCTGGCTGACTGGGAAGTGG |
| rat | TGF-β1 | CCGCAACAACGCAATCTATG | GCACTGCTTCCCGAATGTCT |
| rat | VEGF | ACCAAAGCCAGCACATAGGA | GGGGCATTAACTGCATCTGG |
| rat | CD206 | GCAGGTGGTTTATGGGATGTTT | TTTGGGTTCAGGAGTTGTTGTG |
| rat | Arginase1 | CACCTGAGTTTTGATGTTGATGG | TCCTGAAAGTAGCCCTGTCTTGT |
| mouse | GAPDH | AACTTTGGCATTGTGGAAGG | GGATGCAGGGATGATGTTCT |
| mouse | IL-6 | CCAAGAACGATAGTCAATTCCA | CATCAGTCCCAAGAAGGCAAC |
| mouse | IL-1β | CAGGATGAGGACCCAAGCAC | TCAGACAGCACGAGGCATTT |
| mouse | TNF-α | CCCTTTACTCTGACCCCTTTATT | TGTCCCAGCATCTTGTGTTTCT |
| mouse | CD206 | TCTCCCGGAACCGACTCTTC | AACTGGTCCCCTAGTGTACGA |

As shown in FIG. 4, increased expression of various proinflammatory cytokines derived from M1 macrophages was seen in the DMEM administration group. In the dental pulp stem cell serum-free culture supernatant administration group, on the other hand, expression of proinflammatory cytokines derived from M1 macrophages was suppressed, while production of various anti-inflammatory cytokines (TGF-β, CD206, Arginase I and IL-10) derived from M2 macrophages was increased.

(5) CD206 Immune Staining Results in Fulminant Hepatitis Model

Figure 5:
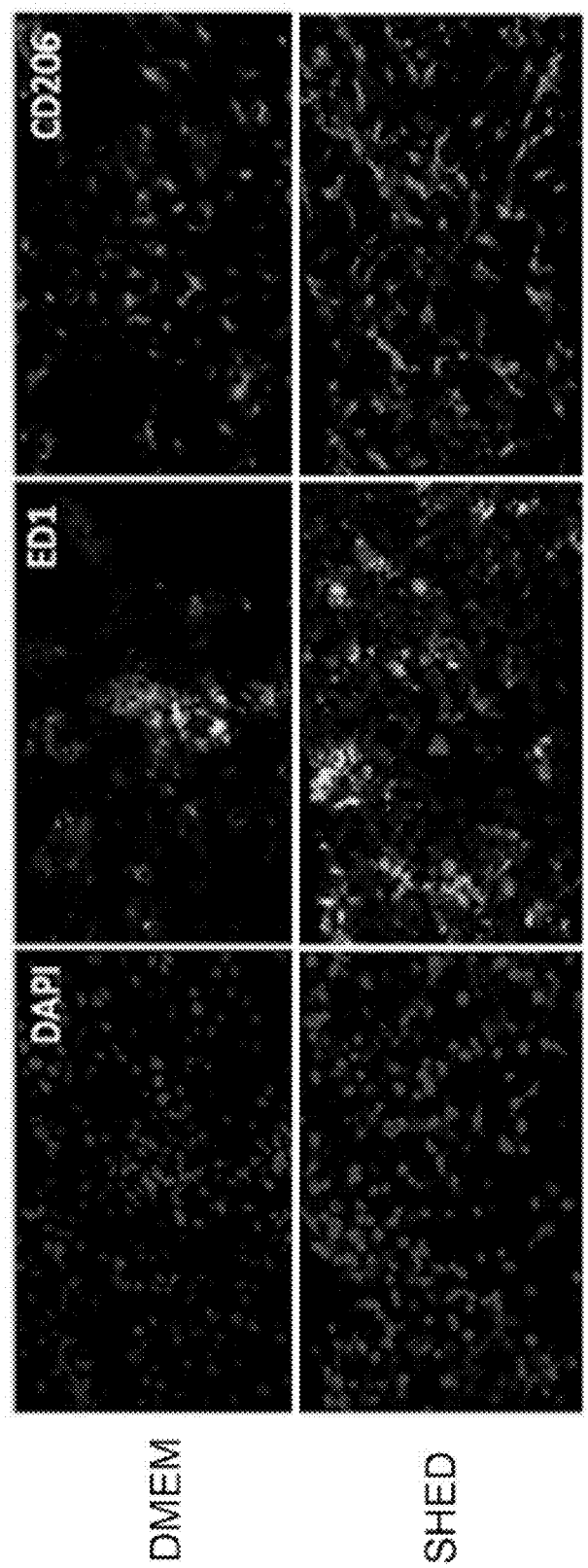
FIG. 5 shows CD206 staining results in fulminant hepatitis model rats.

FIG. 5 shows the results of CD206 staining of the tissue of the fulminant hepatitis model in the dental pulp stem cell serum-free culture supernatant administration group and control group. As shown in FIG. 5, CD206 expression was conspicuous in the dental pulp stem cell serum-free culture supernatant administration group, clearly indicating expression of M2 macrophages.

Example 3

In this example, the therapeutic usefulness of dental pulp stem cells was analyzed using a pulmonary fibrosis model animal.

(1) Preparation of Pulmonary Fibrosis Model Mice

A Bleomycin hydrochloride solution for inducing severe lung damage was prepared by dissolving 6 U/kg in physiological saline. This solution was administered intratracheally to female C57BL/6J mice (6 to 8 weeks, 17 to 20 g). After 24 hours, induction of lung damage was confirmed by listening for Velcro rale, after which human dental pulp stem cell-derived serum-free culture supernatant, myeloid stem cell serum-free culture supernatant and 500 μl of DMEM were each administered intravenously through the jugular veins, and clinical improvement was confirmed. Weight measurement results are shown in FIG. 6, and survival rates in FIG. 7.

Figure 6:
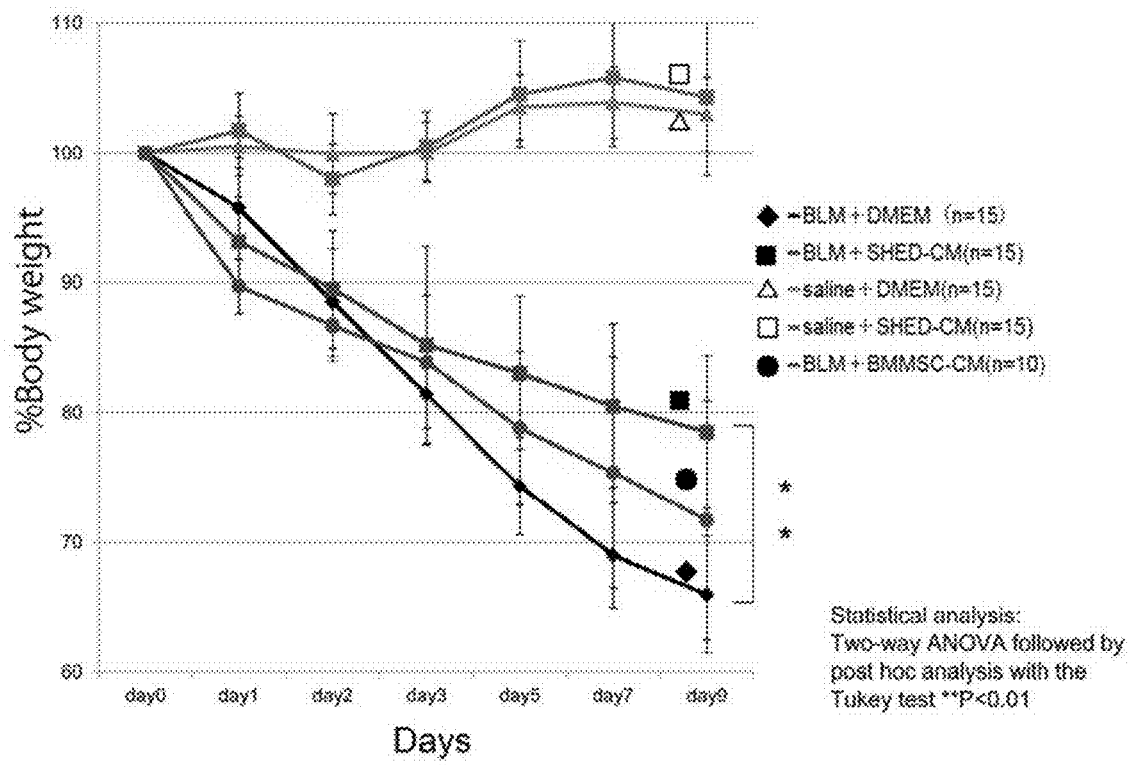
FIG. 6 shows body weight measurement results for pulmonary fibrosis model mice.
Figure 7:
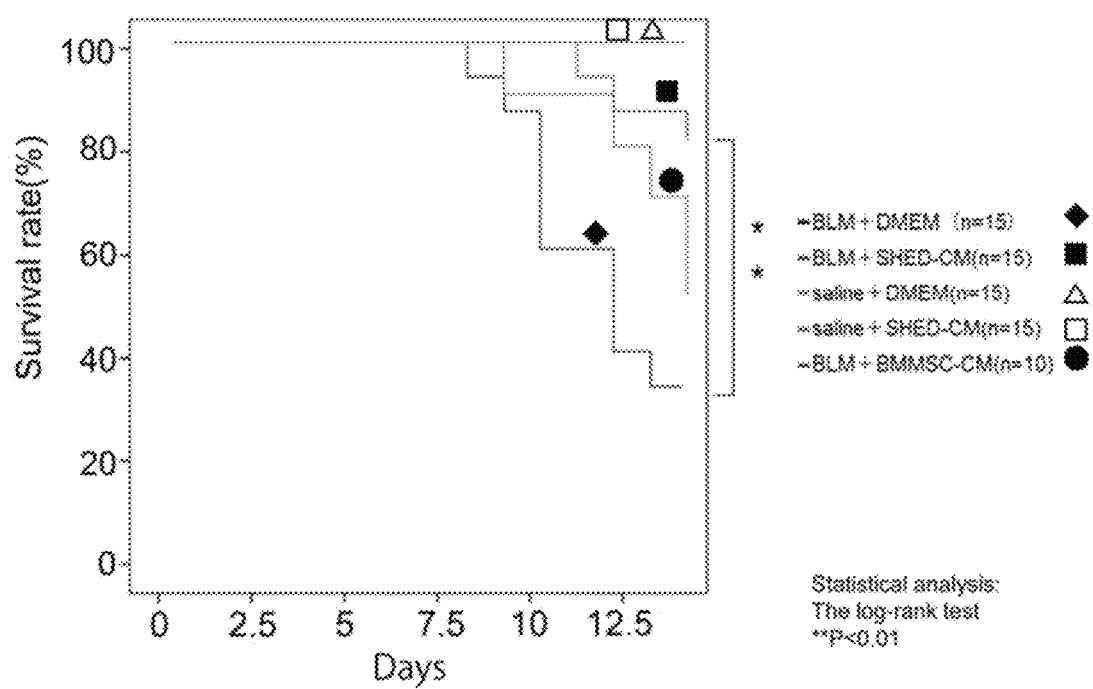
FIG. 7 shows survival rates for pulmonary fibrosis model mice.

(2) Evaluation of Lung Damage by Survival Rate and Body Weight in Pulmonary Fibrosis Model Mice As shown in FIG. 6 and FIG. 7, intratracheal administration of Bleomycin hydrochloride solution to female C57BL/6J mice (17 to 20 g) caused severe lung damage, and the survival rate fell to 33% after 14 days, while body weights fell to 66% after 9 days.

(3) Analysis of Therapeutic Effects of Dental Pulp Stem Cell Serum-Free Culture Supernatant Based on Survival Rates and Body Weights As shown in FIG. 6 and FIG. 7, dramatic clinical improvements were seen only in the group receiving intravenous administration of the dental pulp stem cell serum-free culture supernatant. The 14-day survival rate was 79.4%, and body weights were only reduced to 78.5%. By contrast, no clinical improvements were seen in the myeloid stem cell-derived serum-free culture supernatant and serum-free medium (DMEM) administration groups. The myeloid stem cell-derived serum-free culture supernatant administration group had a survival rate of 50% and a weight ratio of 71.7%. The DMEM administration group had a survival rate of 33.3% and a weight ratio of 66%.

(4) Pathological Analysis in Pulmonary Fibrosis Model Mice

Widespread thickening of the supporting (interstitial) tissue of the lungs due to inflammation is seen in the lungs of acute pulmonary disease patients. In the model mice in this case, pathology was evaluated by observing these factors. Fibrosis of pulmonary tissue was evaluated by HE staining and Masson trichrome (MT) staining, a specific staining method for connective tissue. The results are shown in FIG. 8.

Figure 8:
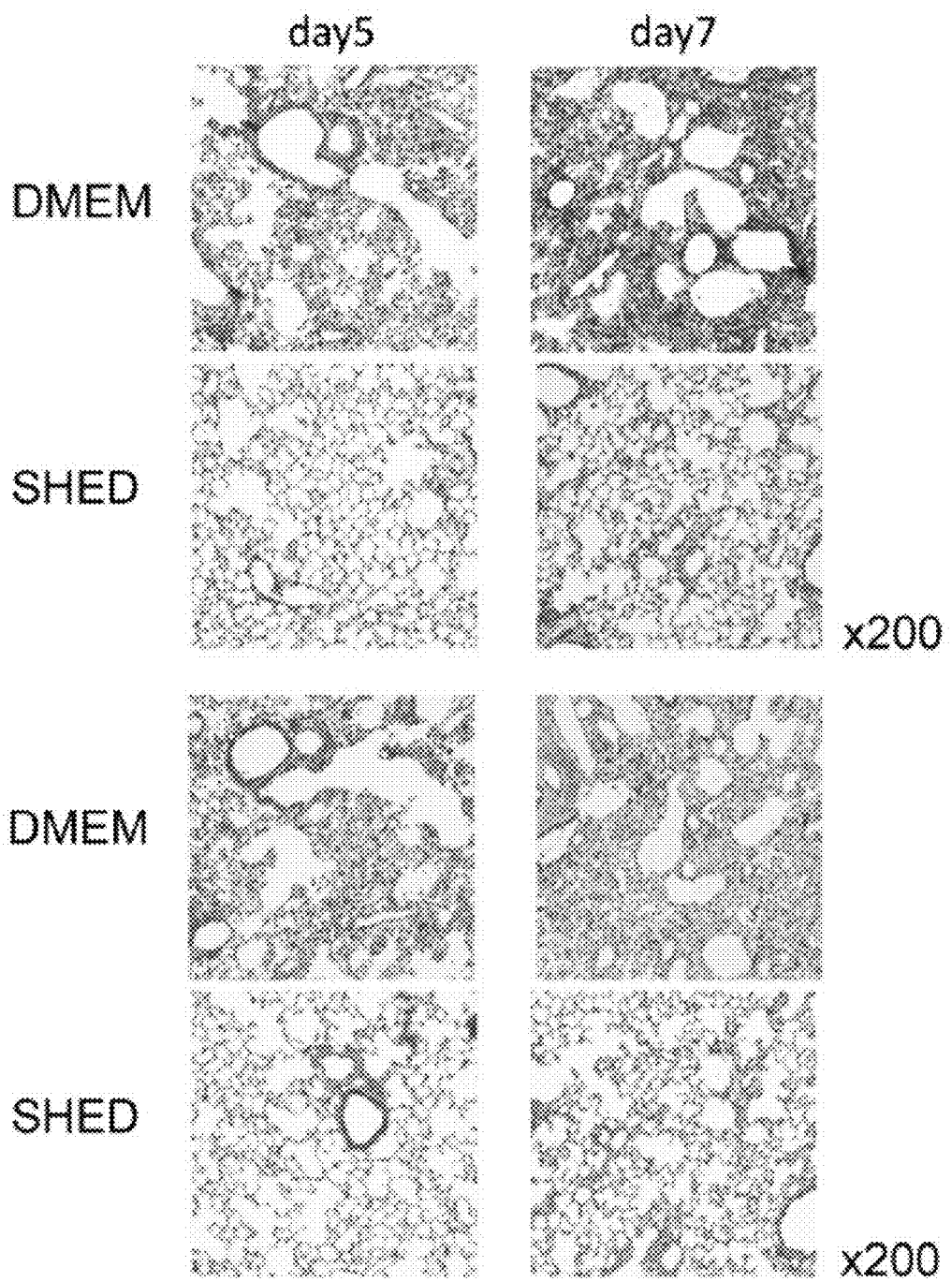
FIG. 8 shows the results (HE stain, MT stain) of a pathological analysis in pulmonary fibrosis model mice.

As shown in FIG. 8, widespread interstitial thickening was observed by HE staining and MT staining in the DMEM administration group, and the MT stain showed a dramatic increase in fibrosis area. 24 hours after administration of dental pulp stem cell-derived serum-free culture supernatant, the tissue image showed normal lung tissue.

(5) Immunohistological Analysis in Pulmonary Fibrosis Model Mice

In severe inflammatory reactions, anti-inflammatory, tissue-regenerating M2 macrophages play an important role in lung tissue repair. Therefore, an M2 macrophage marker called mannose receptor CD206 was measured by immune staining in the dental pulp stem cell-derived serum-free culture supernatant administration group and the DMEM group 48 hours after induction of acute lung damage. The results are shown in FIG. 9.

Figure 9:
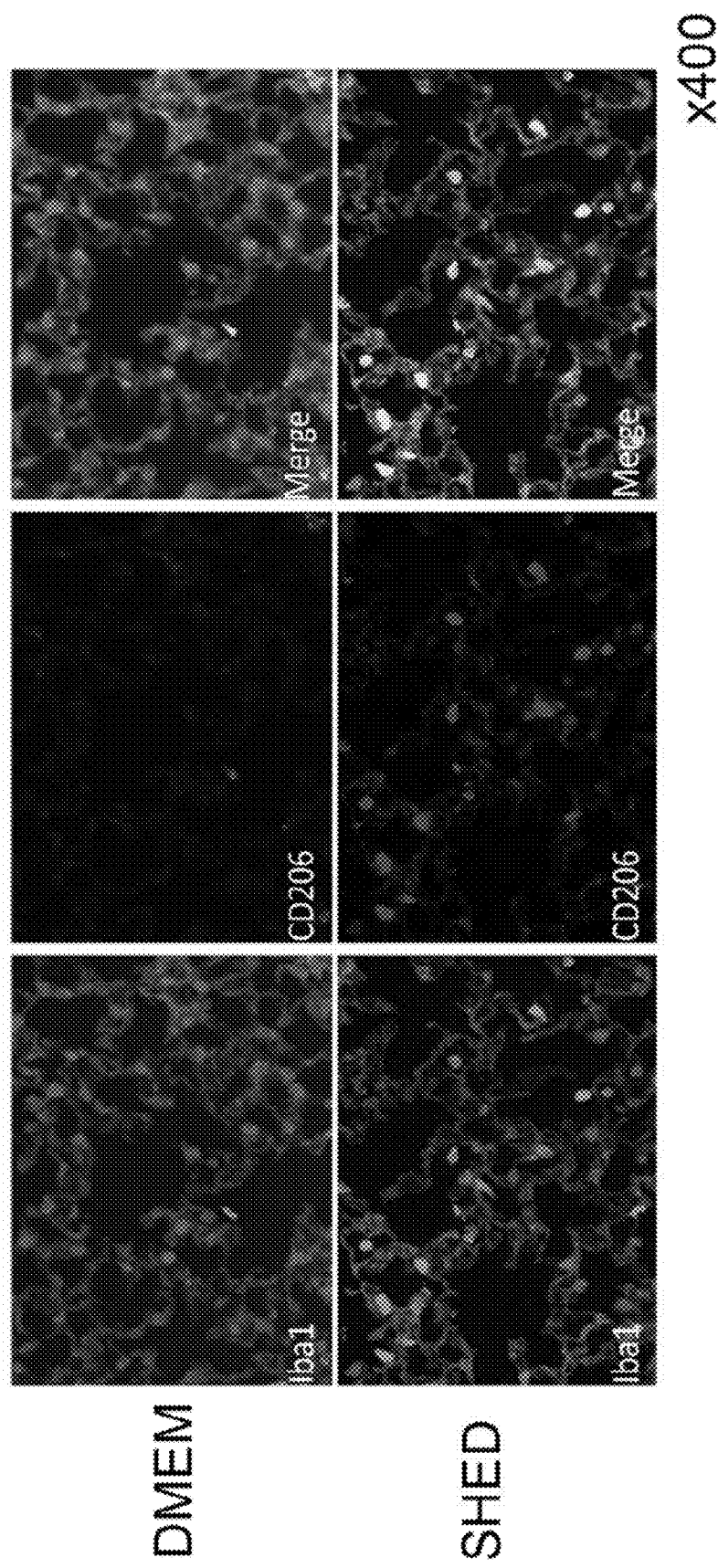
FIG. 9 shows the results of an immunohistological analysis in pulmonary fibrosis model mice.

As shown in FIG. 9, a dramatic increase in CD206-positive cells was seen in the dental pulp stem cell serum-free culture supernatant administration group in contrast with the DMEM administration group.

Example 4

In this example, the therapeutic usefulness of dental pulp stem cell culture supernatant administration for hepatic cirrhosis was analyzed.

(1) Preparation of Hepatic Cirrhosis Model Mice

Carbon tetrachloride ($CCl_4$) was dissolved at a rate of 1.0 ml/kg in olive oil to prepare a drug for inducing liver damage, which was then administered intraperitoneally twice a week continuously for 4 weeks to C57BL6 mice (20 to 25 g) to prepare hepatic cirrhosis model mice. 24 hours after the final carbon tetrachloride administration (1 month after the start of carbon tetrachloride administration), 500 µl of the (serum-free) dental pulp stem cell culture supernatant (SHED-CM) prepared in Example 1 was administered intravenously once, and clinical improvement was verified. DMEM was administered in the same way as a control.

(2) Pathological Analysis in Hepatic Cirrhosis Model

Liver cell death, inflammatory cell infiltration and widespread increases in irreversible fibrotic tissue are observed in the livers of hepatic cirrhosis and chronic hepatitis patients. A tissue analysis was therefore performed 3 days after SHED-CM administration. The results are shown in FIG. 10 and FIG. 11.

Figure 10:
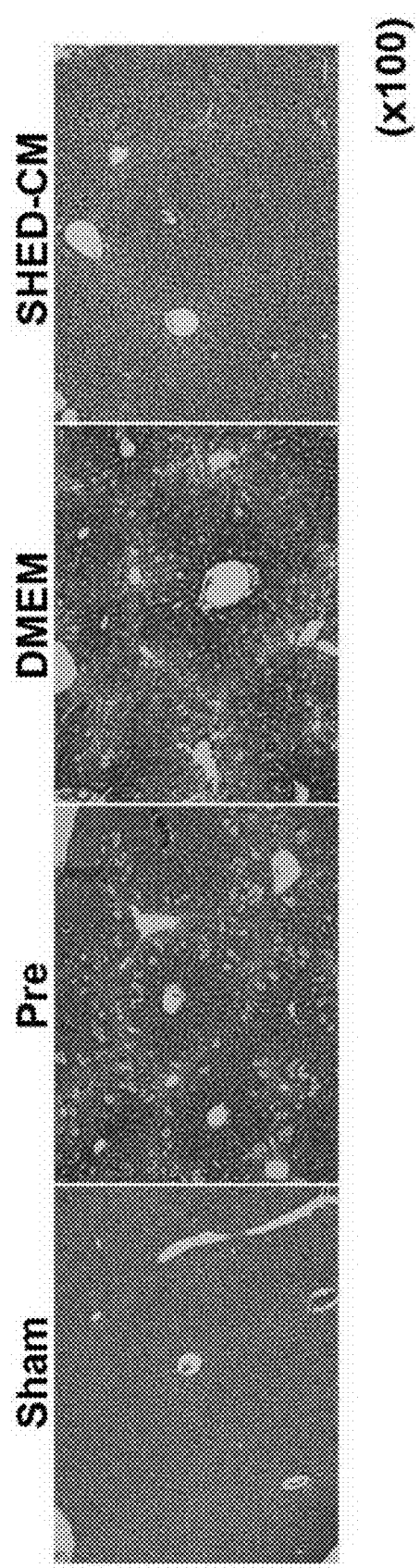
FIG. 10 shows the results (HE stain) of a tissue analysis of the livers of hepatic cirrhosis model mice after SHED-CM administration.

As shown in FIG. 10, while the Sham mouse exhibited normal liver tissue in HE staining, many dead liver cells were observed in the pre-treatment mouse (before SHED-CM administration), along with advanced fibrosis in the space of Disse. Severe cell infiltration and advanced fibrosis were observed in the DMEM administration group. By contrast, the images in the SHED-CM administration group showed nearly normal liver tissue.

Figure 11:
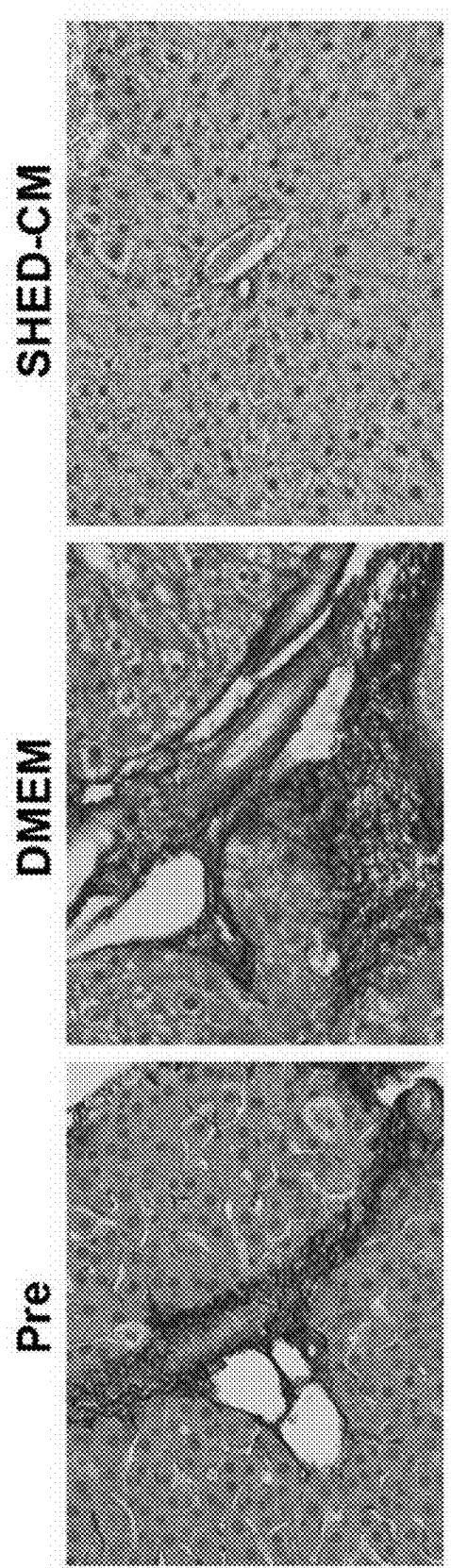
FIG. 11 shows the results (Sirius red stain) of a tissue analysis of the livers of hepatic cirrhosis model mice after SHED-CM administration.

Moreover, as shown in FIG. 11, the Sirius red stain (red stain: cellulose stain) showed severe fibrosis in the pre-treatment and DMEM administration group. Almost no fibrosis was observed in the SHED-CM administration group.

(3) Gene Analysis in Liver Cirrhosis and Chronic Hepatitis Model

RNA was collected from liver tissue 3 days after DMEM and SHED-CM administration, and gene expression of proinflammatory cytokines and the like was analyzed by quantitative PCR. The results are shown in FIG. 12 and FIG. 13.

Figure 12:
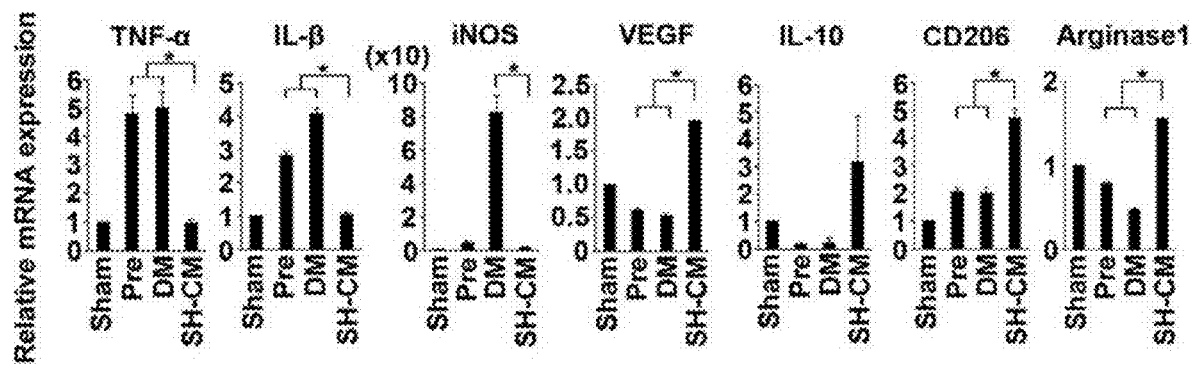
FIG. 12 shows the results of a gene analysis of liver tissue following SHED-CM administration to hepatic cirrhosis model mice.

As shown in FIG. 12, while expression of TNF-α produced by inflammation-promoting M1 macrophages was increased in the DMEM administration group, expression of the anti-inflammatory M2 macrophage markers CD206 and Arginase-1 was increased in the SHED-CM administration group.

Figure 13:
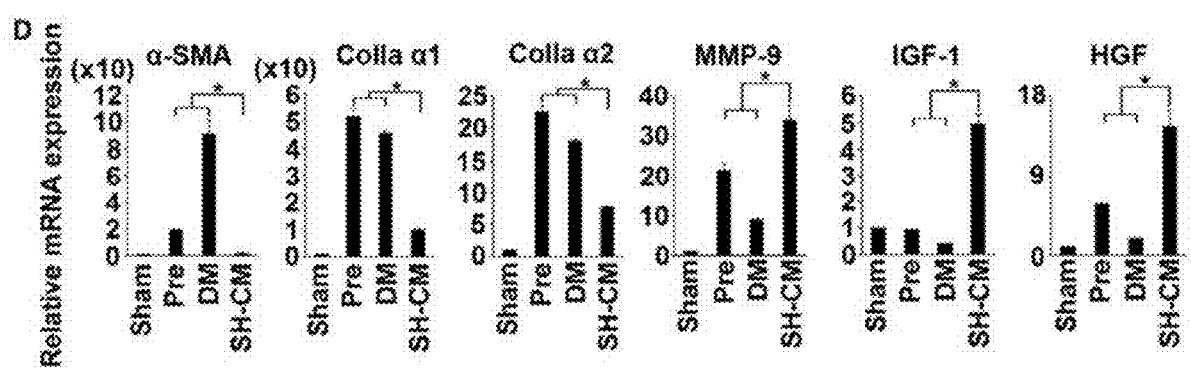
FIG. 13 shows the results of a gene analysis of liver tissue following SHED-CM administration to hepatic cirrhosis model mice.

Moreover, as shown in FIG. 13, expression of α-smooth muscle actin (α-SMA) and Collagen α1 produced by activated hepatic astrocytes increased in the DMEM administration group, while the expression levels of factors associated with liver regeneration, including IGF-1, HGF and matrix metalloprotease-9 (MMP-9), which is associated with fibrolysis, were increased in the SHED-CM administration group.

Figure 14:
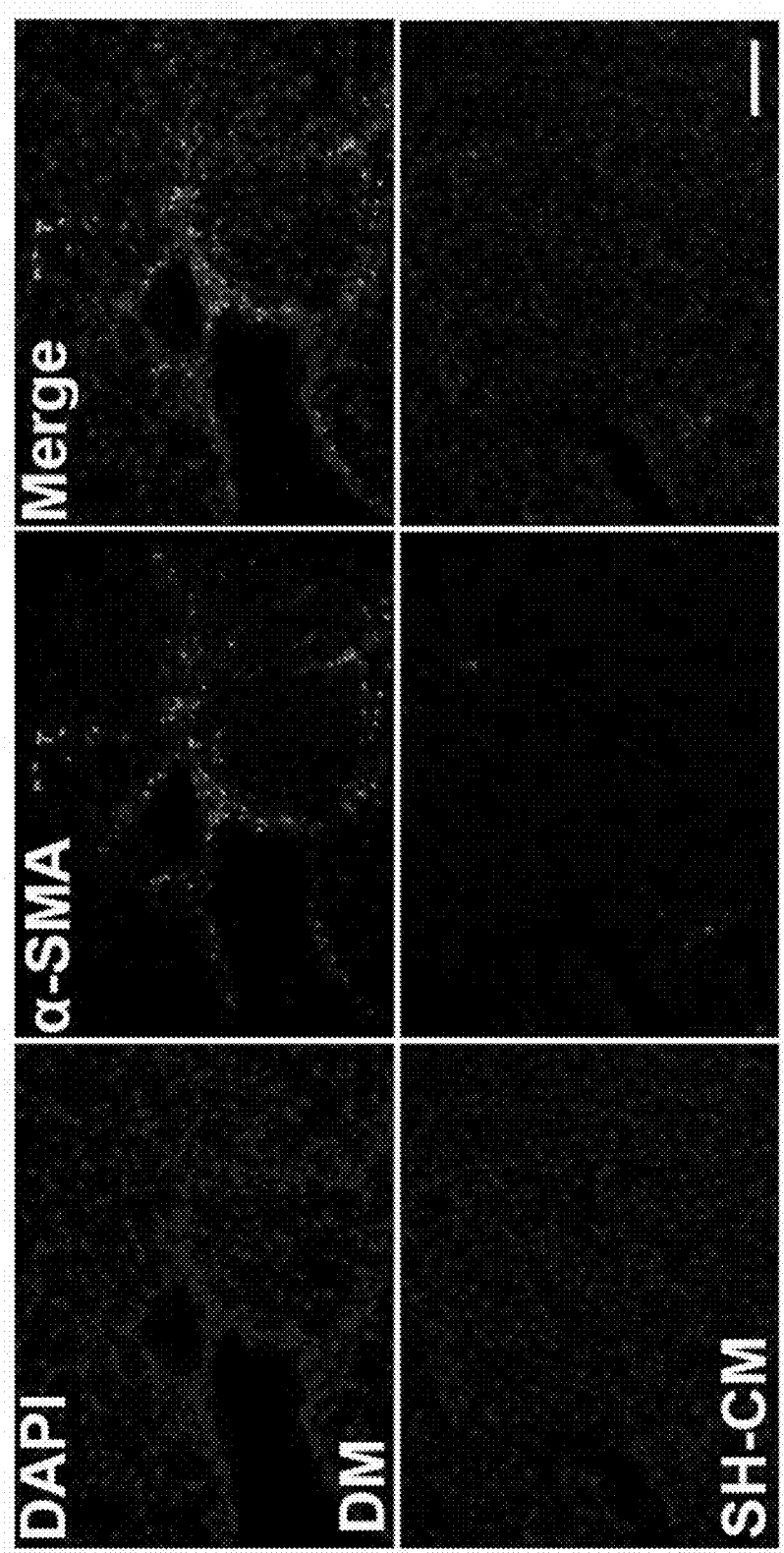
FIG. 14 shows staining results for α-SMA, a marker of activated hepatic astrocytes, in liver tissue following SHED-CM administration to hepatic cirrhosis model mice.

Moreover, as shown in FIG. 14, the staining results for the activated hepatic astrocyte marker α-SMA showed a decrease in the number of α-SMA-positive cells in the SHED-CM administration group. Clearly, the number of activated hepatic astrocytes was dramatically decreased in the SHED-CM administration group.

Example 5

In this example, the usefulness of dental pulp stem cell culture supernatant administration for ischemic heart disease was analyzed.

(1) Preparation of myocardial ischemia reperfusion model mouse 8 to 12 week old male C57BL6/J mice were subjected to general anesthesia by intraperitoneal administration of pentobarbital (50 mg/kg), the four limbs were fixed in the supine position, and intratracheal intubation was performed with 22G Teflon tubes, which were connected to a small animal artificial respirator (respiration rate 150/minute, volume 0.2 mL/time). Thoracotomy was performed through the third left intercostal space, and the left anterior descending coronary artery (LAD) was ligated with nylon thread under a stereoscopic microscope. After 30 minutes the nylon thread was untied and the blood was reperfused.

(2) SHED-CM Administration

At the time of reperfusion, 500 µL, of the SHED-CM prepared in Example 1 was administered once. 500 µL of DMEM was administered to the control group.

(3) Evaluation of Infarct Zone 24 hours after reperfusion, the LAD was again ligated, and perfusion was performed with 1 mL of Evan's blue liquid. The hearts were removed, and transverse sections were prepared and reacted for 20 minutes with 2,3,5-triphenyl tetrazolium chloride (TTC) solution. The left ventricles (LV), critical regions (AAR) and infarct zones (IA) were thus distinguished, and the areas of each were measured with image analysis software. The results are shown in FIG. 15.

Figure 15:
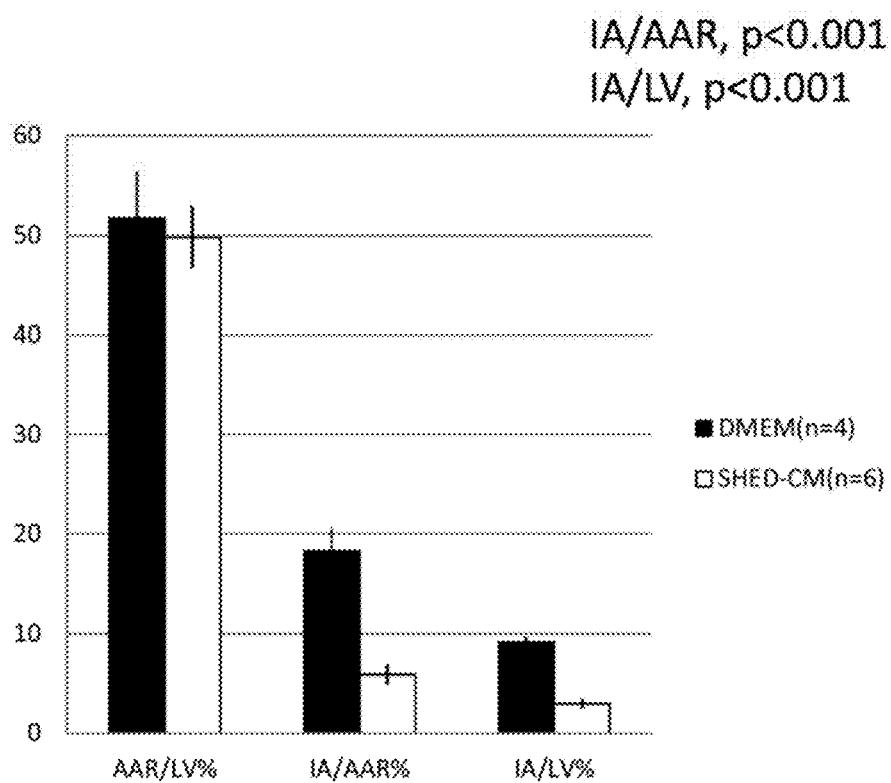
FIG. 15 shows the results of an evaluation of infarct zones following SHED-CM administration to myocardial ischemia reperfusion model mice.

As shown in FIG. 15, the area of the critical region as a percentage of the left ventricle (AAR/LV) was confirmed to be the same in the SHED-CM administration group and control group. In comparison with the control group, the area of the infarct zone as a percentage of the critical region (IA/AAR) and the area of the infarct zone as a percentage of the left ventricle (IA/LV) were both shown to be significantly lower in the SHED-CM group.

(4) Evaluation of Blood Cardiac Troponin Values

Figure 16:
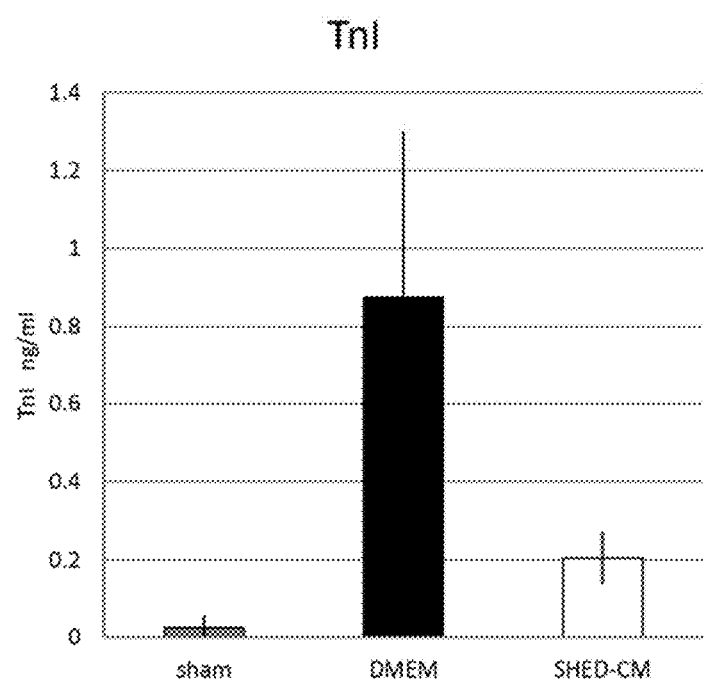
FIG. 16 shows evaluation results for amount of cardiac troponin in plasma following SHED-CM administration to myocardial ischemia reperfusion model mice.

Total blood was taken from mice 24 hours after reperfusion, and cardiac troponin I in plasma was measured by ELISA as a marker of cardiac tissue damage. The results are shown in FIG. 16. As shown in FIG. 16, the cardiac troponin values in model mouse plasma clearly tended to be lower in the SHED-CM group than in the control group.

(5) Evaluation of Proinflammatory Cytokines in Tissue

Figure 17:
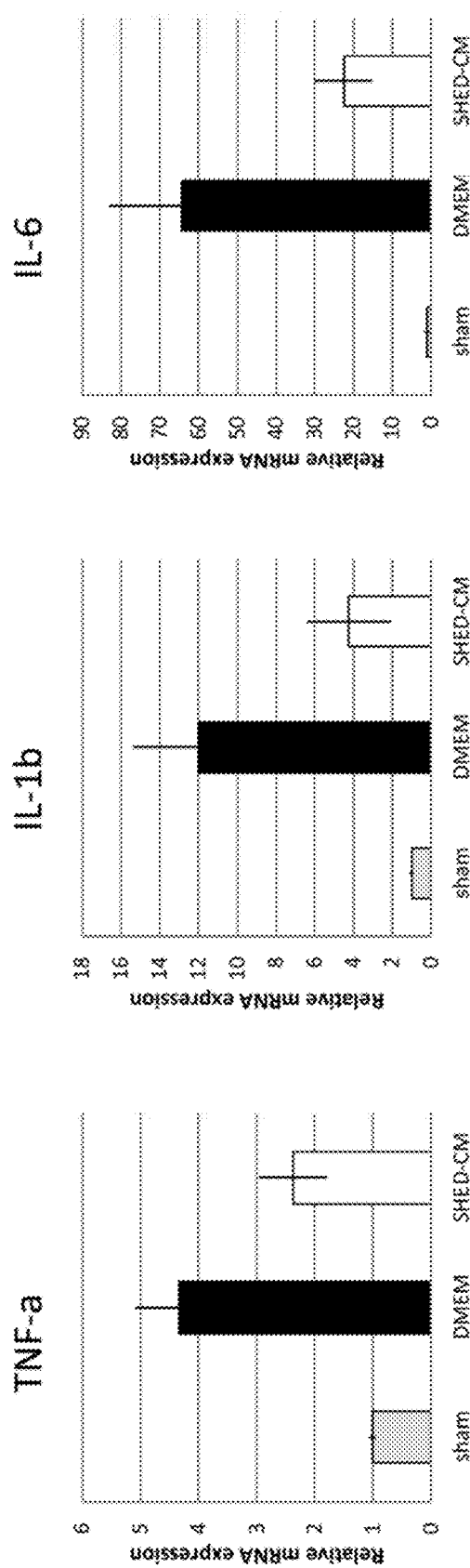
FIG. 17 shows the results of a gene expression analysis in ischemic areas following SHED-CM administration to myocardial ischemia reperfusion model mice.

RNA was extracted from the ischemic areas of hearts removed 24 hours after reperfusion. Gene expression of proinflammatory cytokines (TNF-α, IL-1β, IL-6) in tissue was evaluated by quantitative real-time PCR. The results are shown in FIG. 17. As shown in FIG. 17, gene expression of proinflammatory cytokines in cardiac tissue tended to be suppressed in the SHED-CM administration group for TNF-α, IL-1β and IL-6.

These results show that administration of SHED-CM after acute myocardial infarction has the effect of reducing the infarct zone by immediately suppressing inflammation when it occurs.

Example 6

In this example, the usefulness of dental pulp stem cell culture supernatant administration for multiple sclerosis was analyzed.

(1) Preparation of Experimental Autoimmune Encephalomyelitis (EAE) Mouse as an Animal Model of Multiple Sclerosis 8-week-old female C57BL/6J mice were immunized by subcutaneous injection of 200 µg of $MOG_{35-55}$ protein administered together with complete Freund's adjuvant to the lower back. 400 ng of pertussis toxin was injected intraperitoneally on days 0 and 2 to prepare EAE mice.

(2) SHED-CM Administration

The degree of paralysis of the mice was observed every day using EAE clinical scoring. The symptoms peaked on the 14th day after immunization, on which 500 µl of the SHED-CM prepared in Example 1 was administered through the caudal veins of the mice while 500 µl of DMEM was administered to the control group, after which paralysis was confirmed up to the 28th day by EAE clinical scoring. On the 28th day the mice were sacrificed and their tissue analyzed.

(3) Evaluation of Paralysis by EAE Scoring

Figure 18:
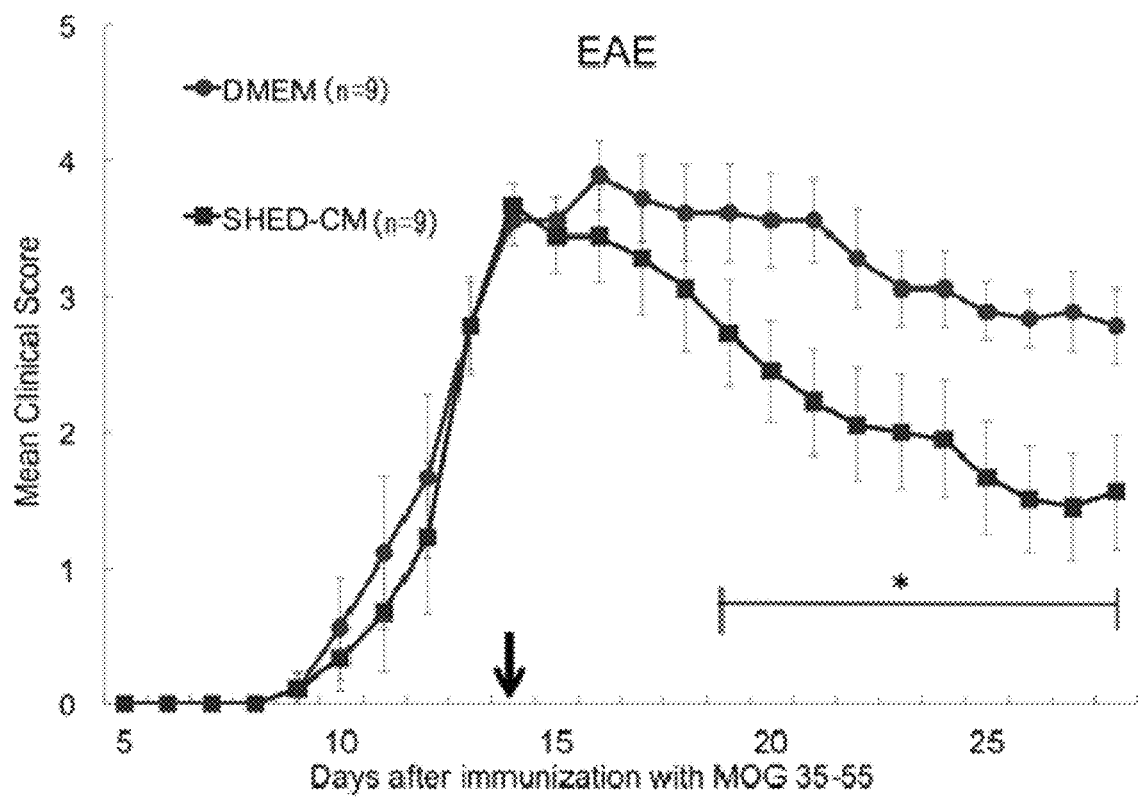
FIG. 18 shows the progress of EAE clinical scores following SHED-CM administration to multiple sclerosis model mice.

Paralysis was evaluated by the following EAE scoring system: 0: normal, 1: tail drooping, 2: debility of hind limbs, 3: incomplete hind limb paralysis, 4: debility of front limbs, complete hind limb paralysis: 5: paralysis of four limbs. The results are shown in FIG. 18. As shown in FIG. 18, significant improvement in paralysis was seen in the SHED-CM administration group beginning on the 19th day after immunization.

(4) Tissue Evaluation

Figure 19:
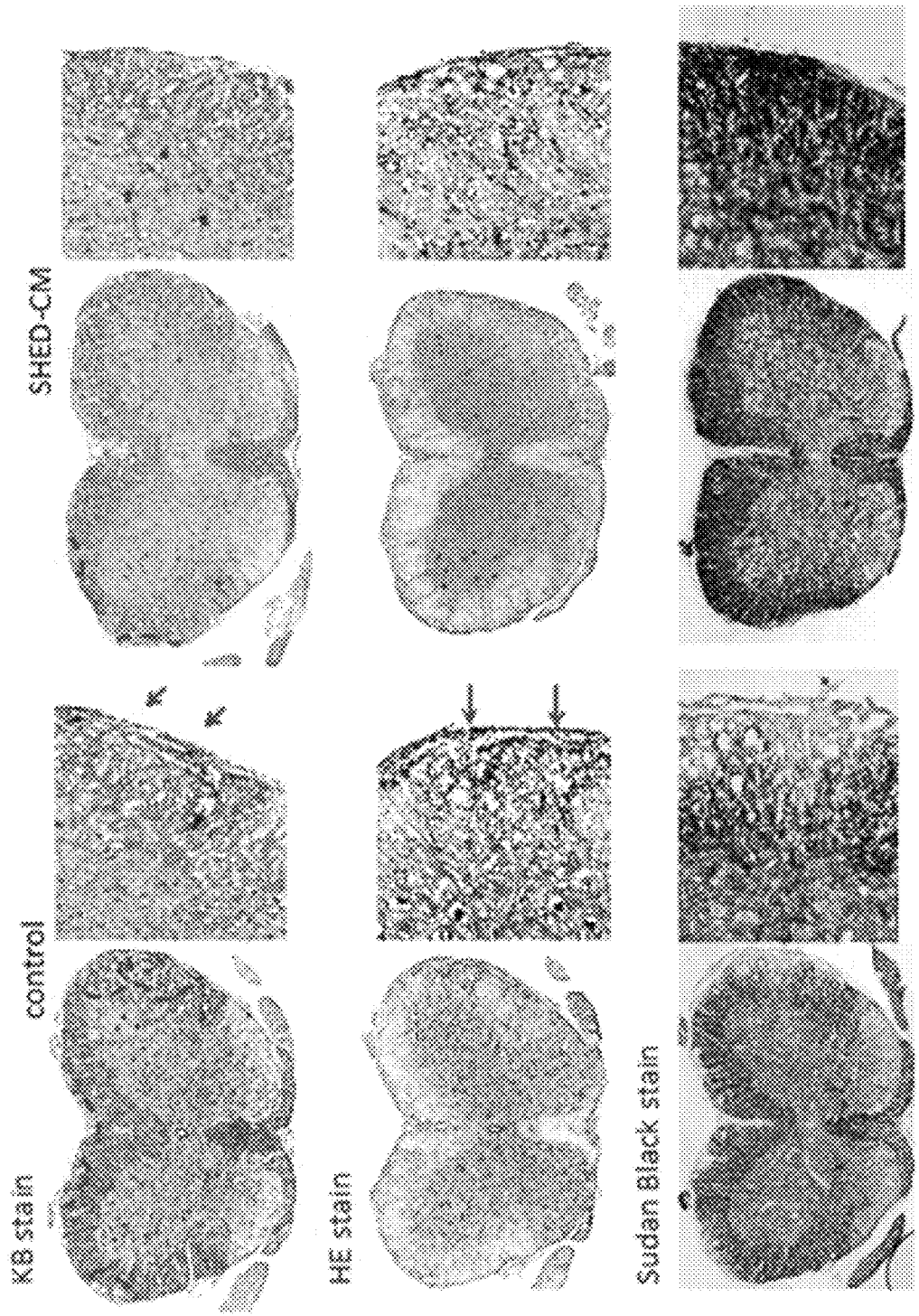
FIG. 19 shows tissue analysis results (HE stain, KB stain, Sudan Black stain) following SHED-CM administration to multiple sclerosis model mice.
Figure 20:
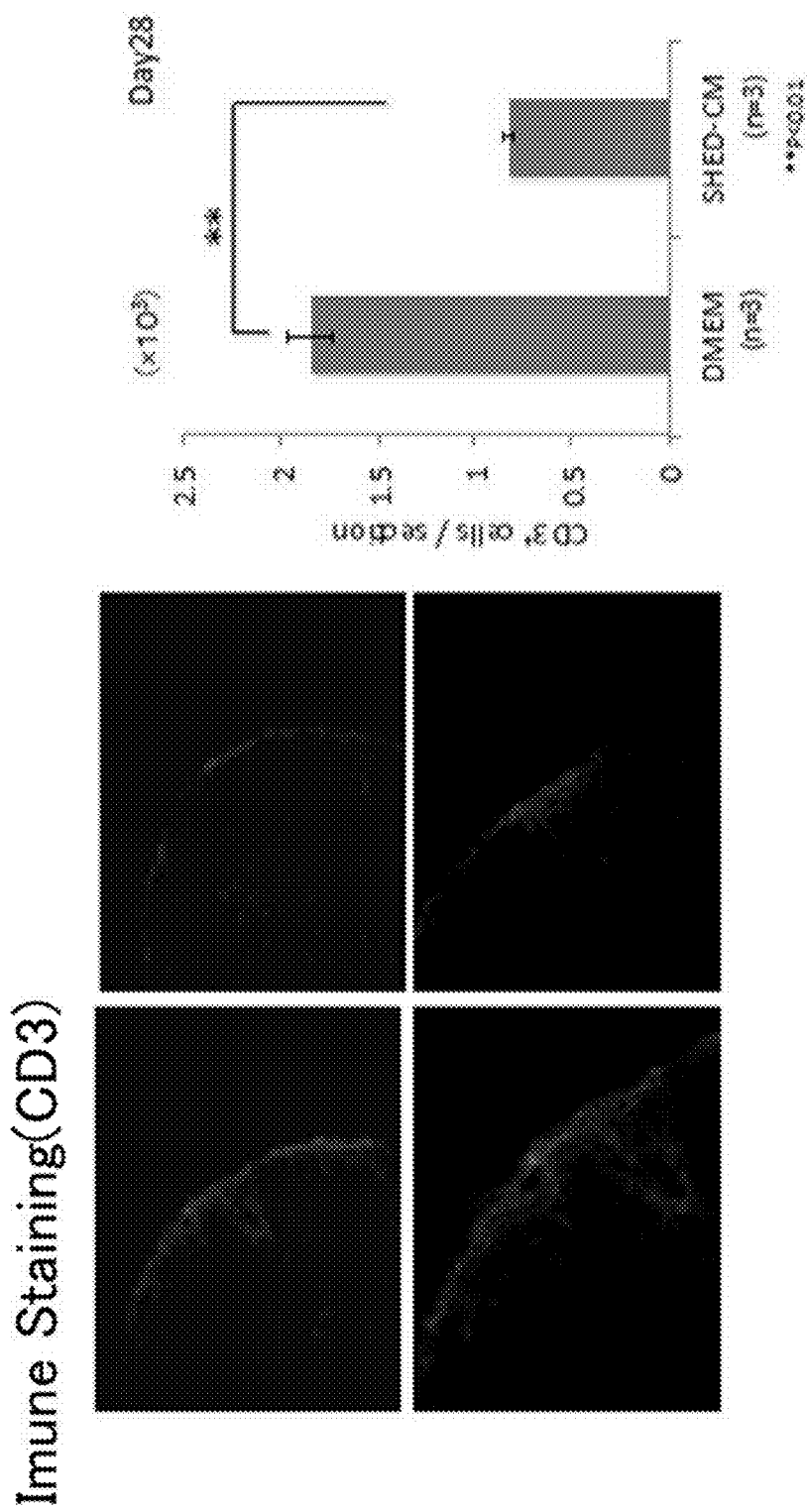
FIG. 20 shows tissue analysis results (CD3 stain) following SHED-CM administration to multiple sclerosis model mice.

A tissue evaluation was performed by HE staining, KB staining, Sudan Black staining or immune staining (CD3: T cells). The results are shown in FIG. 19 and FIG. 20. As shown in FIG. 19, the KB stain and Sudan Black stain showed a reduction in demyelination in the SHED-CM administration group in comparison with the control group, and infiltrating cells were also reduced. A reduction in infiltrating cells was also shown by HE staining. As shown in FIG. 20, moreover, the immune staining showed a reduction in the number of infiltrating T-cells in the SHED-CM administration group.

These results show that SHED-CM can improve condition in cases of inflammatory autoimmune disease.

Example 7

In this example, the usefulness of dental pulp stem cell culture supernatant administration for human systemic lupus erythematosus (SLE) was analyzed.

(1) Preparation of Experimental Autoimmune Encephalomyelitis (SLE) Mouse as an Animal Model of Human SLE Multiple Sclerosis Using MRL-1 pr/1 pr, a human SLE model mouse, the levels of anti-ds-DNA IgG antibody in peripheral blood serum were measured as a clinical marker of human SLE at 15 weeks of age, and satisfactory occurrence of SLE symptoms was confirmed.

(2) SHED-CM Administration

At 16 weeks, 500 µl per mouse of the SHED-CM prepared in Example 1 was injected through the external jugular vein. At 20 weeks the mice were killed, and the kidneys, spleens, axillary lymph nodes, urine and peripheral blood serum were collected.

(3) Evaluation of Immune Suppression

The immune suppression effects of dental pulp stem cell culture supernatant was evaluated by quantifying the level of anti-ds-DNA IgG antibody in peripheral blood serum and the amount of immune complexes in a lysate of homogenized kidney by ELISA. Spleen weights were also measured, a SI was prepared as in the literature (Ito T, Seo N, Yagi H, et al: Unique therapeutic effects of the Japanese-Chinese herbal medicine Sairei-to on Th1/Th2 cytokines balance of the autoimmunity of MRL/1 pr mice. J Dermatol Sci. 28: 198-210, 2002), and the degree of spleen enlargement was observed. Kidney HE staining was also performed, the amount of protein in the collected urine was measured, and changes in kidney function were observed.

Figure 21:
FIG. 21 shows spleens following SHED-CM administration to human SLE model mice.
Figure 21:
Figure 22:
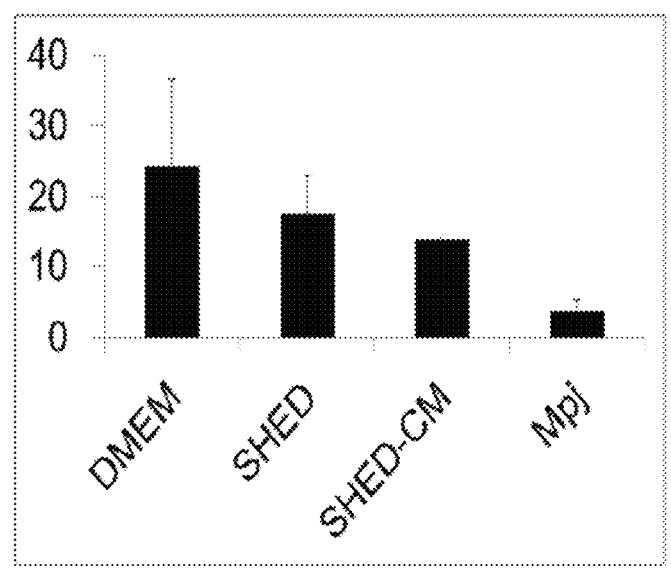
FIG. 22 shows the results of a comparison of spleen weights following SHED-CM administration to human SLE model mice.

Spleen enlargement and spleen weights are shown in FIG. 21 and FIG. 22. As shown in these figures, enlargement of the spleen occurred as the symptoms worsened, but in comparison with the DMEM group the spleen weights and sizes were similar to those of normal spleens in the SHED-CM administration groups, indicating a tendency to suppress spleen enlargement.

Figure 23:
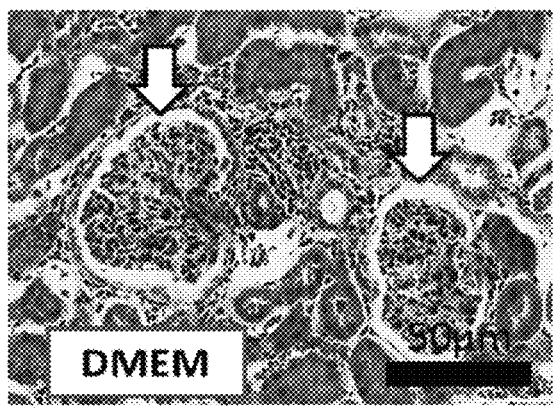
FIG. 23 shows the results of HE staining of spleen tissue sections following SHED-CM administration to human SLE model mice.
Figure 23:
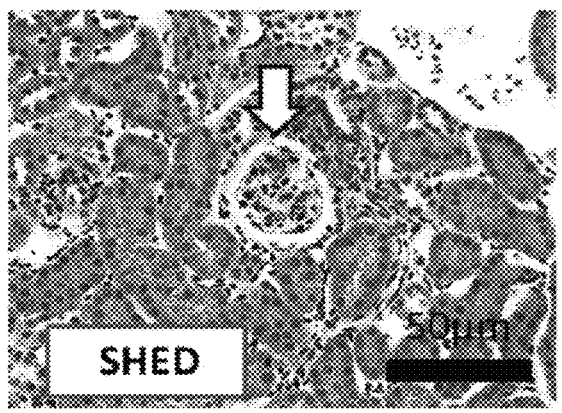
Figure 23:
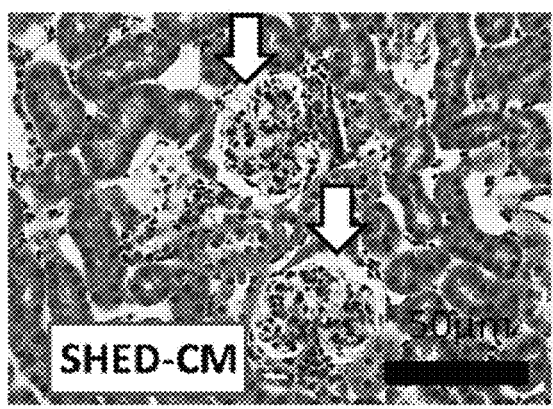

FIG. 23 shows HE stains of tissue sections. As shown in FIG. 23, cell proliferation is seen in association with kidney inflammation, but in comparison with the DMEM administration group the glomeruli appear more similar to normal glomeruli in the SHED-CM administration group, indicating improvement in kidney inflammation.

Figure 24:
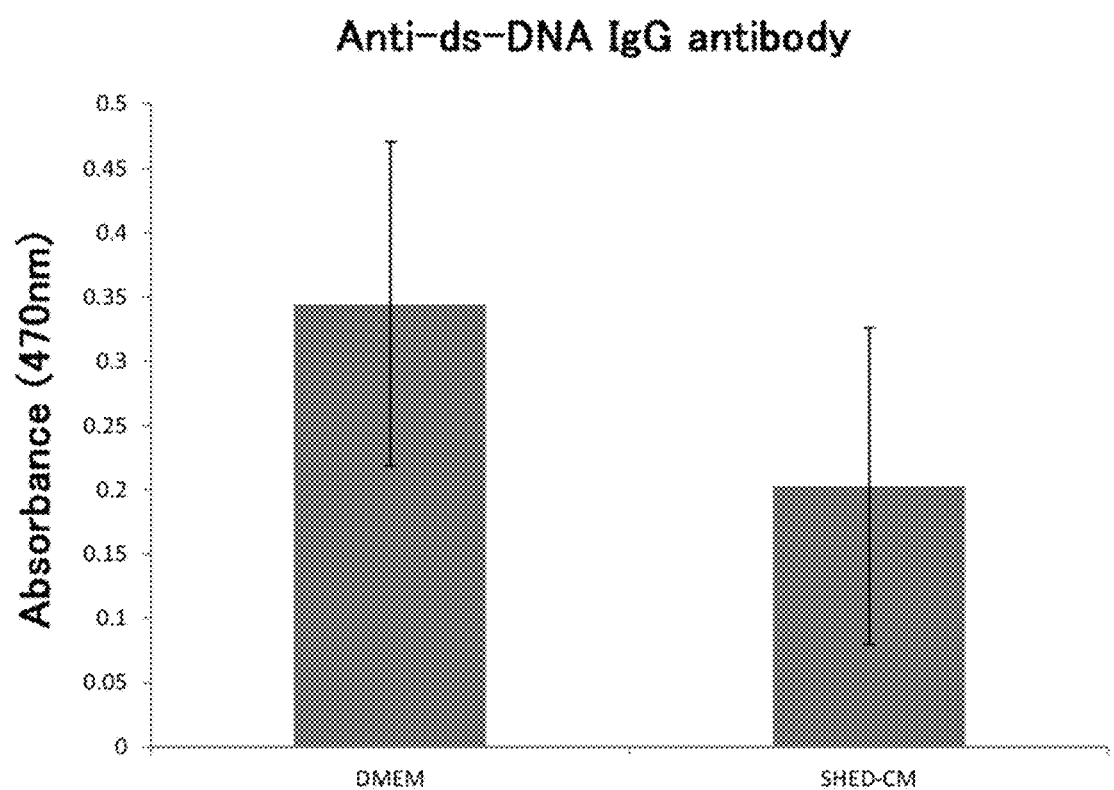
FIG. 24 shows anti-ds-DNA IgG antibody volume in blood following SHED-CM administration to human SLE model mice.

Moreover, FIG. 24 shows the results of an ELISA measurement of anti-ds-DNA IgG antibody in blood using peripheral blood serum. As shown in FIG. 24, the amount of anti-ds-DNA IgG antibody in blood tended to be lower in the SHED-CM administration group than in the DMEM administration group.

These results show that SHED-CM administration is useful for SLE.

Example 8

In this example, the usefulness of dental pulp stem cell culture supernatant for rheumatoid arthritis was analyzed.

(1) Preparation of Collagen Antibody-Induced Arthritis Model Mice

Arthritis-causing antibodies were administered intraperitoneally to 8-week-old male DBA/1J mice to cause arthritis. 3 days later LPS was administered intraperitoneally to exacerbate the arthritis. Inflammation peaked 7 to 10 days after antibody administration.

(2) SHED-CM Administration

A single 500 µl dose of the SHED-CM prepared in Example 1 was administered to the caudal vein on the 5th day after antibody administration. The control group received a single 500 µl administration of DMEM.

(3) Arthritis Score Evaluation

The arthritis scores of the four limbs were measured for 14 days beginning on the day of antibody administration. Three sites were observed, the toes, arches and ankles, and the number of joints where swelling was observed in each was scored (score 1 to 3). A score of 4 was given if extremely severe swelling was observed at all three sites. These were observed for all four limbs, so the maximum score for each mouse was 16. The results are shown in FIG. 25.

Figure 25:
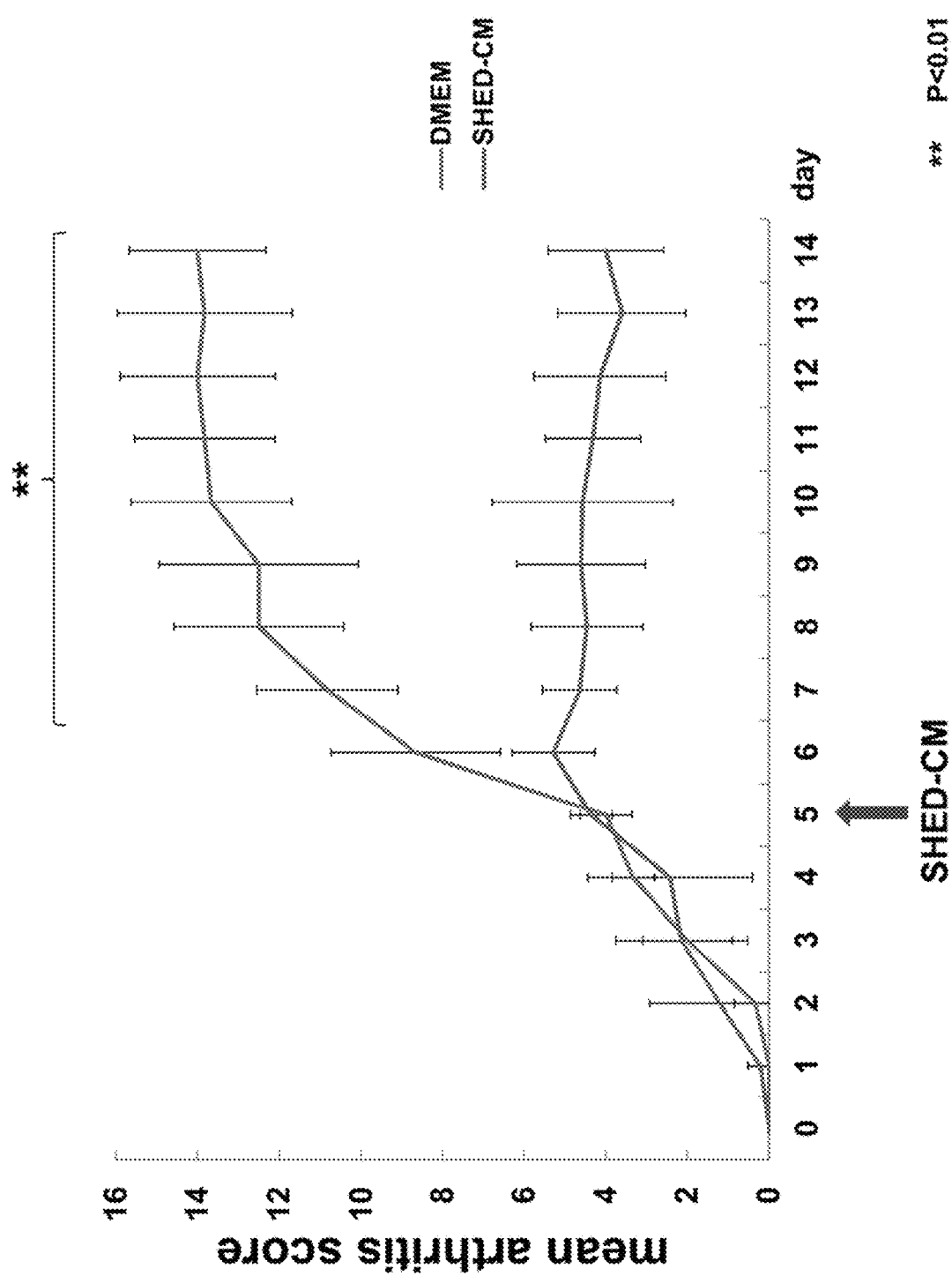
FIG. 25 shows the progress of arthritis scores following SHED-CM administration in arthritis model mice.

As shown in FIG. 25, the arthritis scores were significantly lower in the SHED-CM administration group than in the control group.

(4) Evaluation of Hind Paw Thickness

Figure 26:
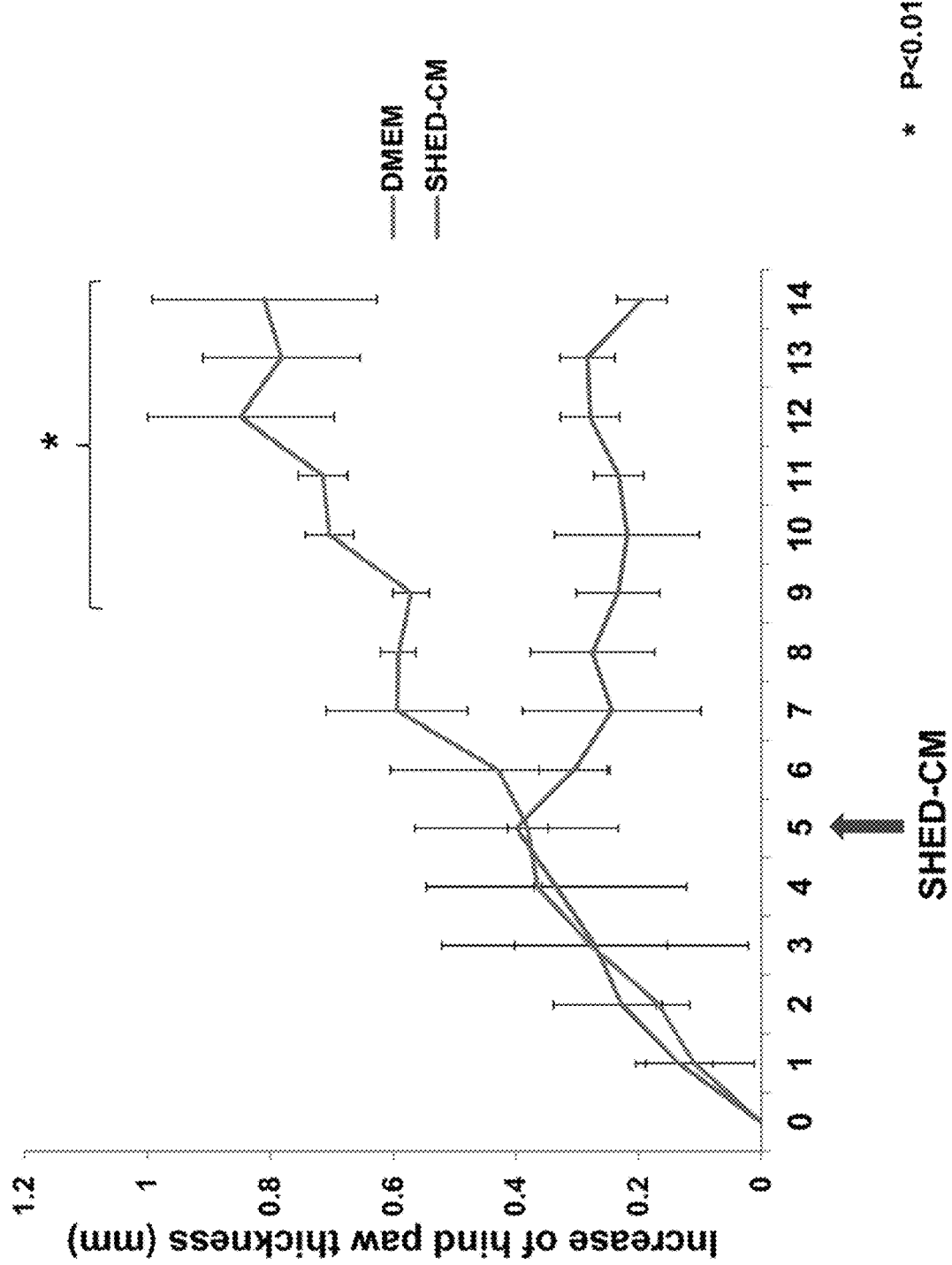
FIG. 26 shows the progress of hind paw thickness following SHED-CM administration in arthritis model mice.

Hind paw thickness was measured on the 14th day after antibody administration. The thicknesses of the arches of both hind paws of the mice were measured with a digital caliper, and the average of the two given as the hind paw thickness for that mouse. The difference between this the hind paw thickness on the day of antibody administration was calculated, and the increase was evaluated. The results are shown in FIG. 26. As shown in FIG. 26, the increase in hind paw thickness was significantly less in the SHED-CM group than in the control group, showing that hind paw swelling due to arthritis was suppressed.

(5) Histological Evaluation

Figure 27:
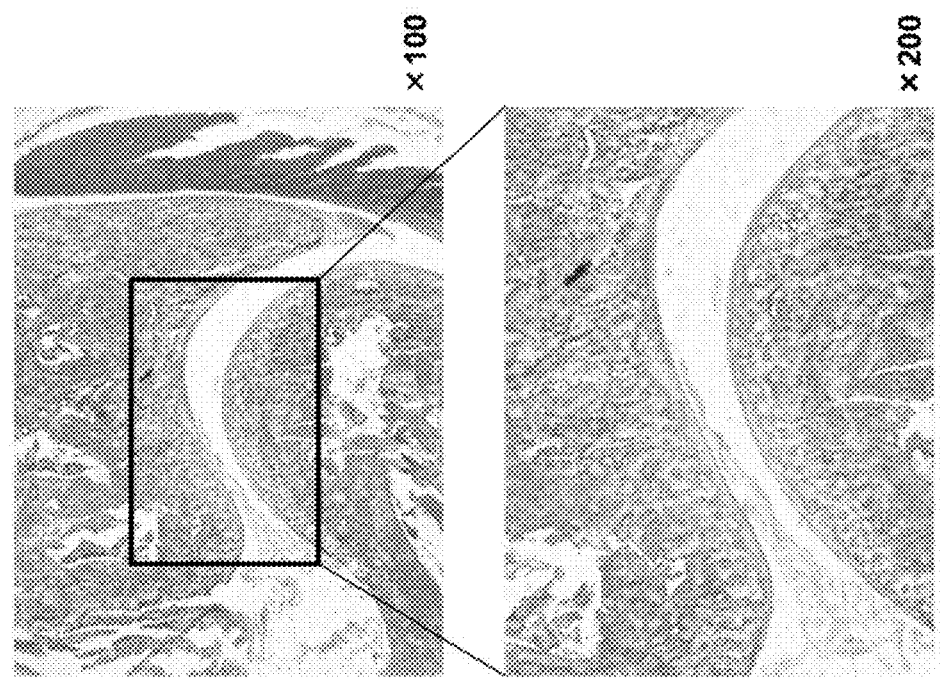
FIG. 27 shows the results of HE staining of ankle tissue sections following SHED-CM administration in arthritis model mice.
Figure 27:
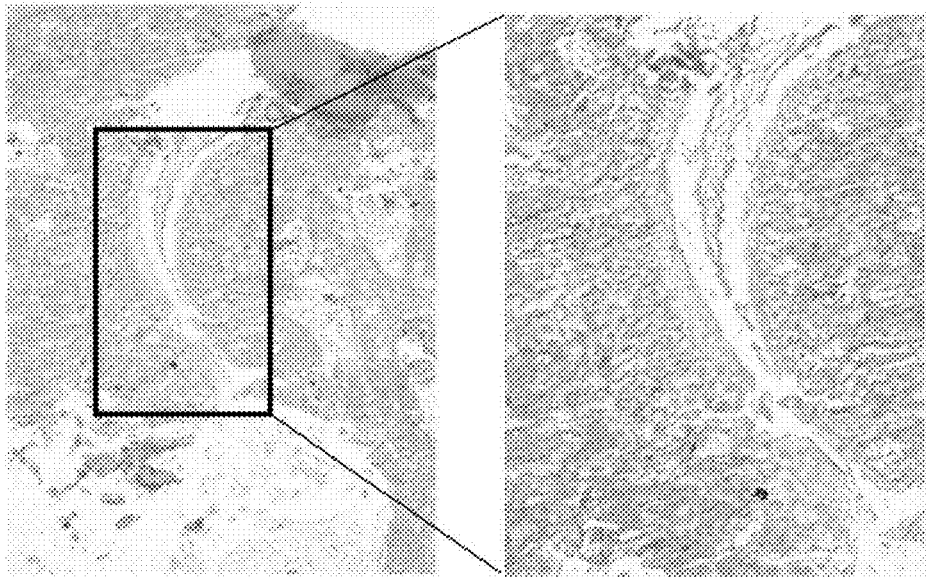
Figure 28:
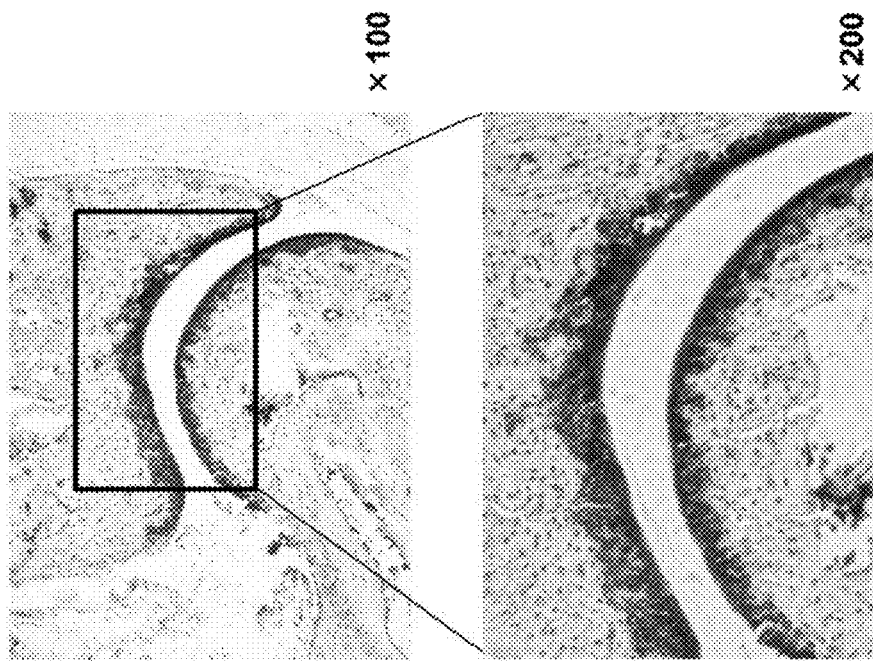
FIG. 28 shows the results of toluidine blue staining of ankle tissue sections following SHED-CM administration in arthritis model mice.
Figure 28:
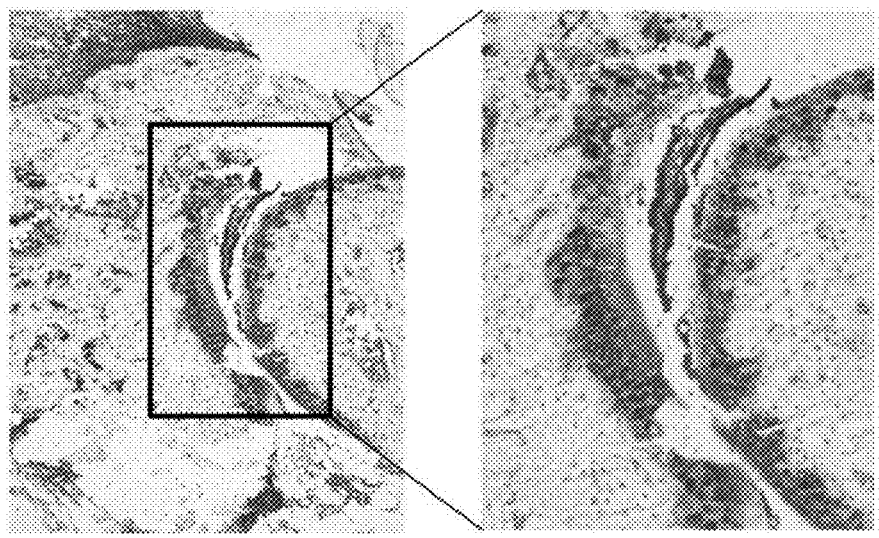

Tissue sections were prepared from the ankles of mice that had been killed on the 14th day after antibody administration, and stained with HE and toluidine blue, and histological changes were evaluated. Inflammatory cell infiltration of the joints, synovial tissue hyperplasia, and the degree of bone destruction on the joint surface were evaluated, and a score was assigned, with a maximum score of 6. The results are shown in FIG. 27 to FIG. 29. As shown in FIG. 27 to FIG. 29, the histological scores were significantly lower in the SHED-CM administration group than in the control group, indicating suppression of inflammatory cell infiltration and tissue destruction in the joints.

(6) Gene Expression Evaluation of Proinflammatory Cytokines and Tissue Degrading Factor in Tissue RNA was extracted from the four limbs of mice that had been killed on the 7th day after antibody administration, and gene expression of proinflammatory cytokines (TNF-α, IL-1β, IL-6) and a tissue-degrading factor (MMP3) was evaluated by real-time quantitative PCR. The results are shown in FIG. 30.

As shown in FIG. 30, gene expression of proinflammatory cytokines and the tissue degrading factor in tissue was significantly lower in the SHED-CM administration group than in the control group for IL-1β, IL-6 and MMP3. A clear suppression tendency also appeared for TNF-α.

These results suggest that SHED-CM has a therapeutic effect on arthritis.

These results show that the composition is useful for the treatment of inflammatory disease in general.

What is claimed:

1. A method of treating an inflammatory disease comprising, administering to a subject in need thereof an effective amount of a composition comprising a culture supernatant, wherein the culture supernatant is obtained by a method comprising
   (1) selecting adherent cells from dental pulp cells, and
   (2) culturing the adherent cells to at least 70% confluence,
   (3) culturing the cells obtained in step (2) in serum-free liquid, and
   (4) obtaining the supernatant,
wherein the composition does not contain dental pulp stem cells, and
wherein the inflammatory disease is selected from the group consisting of fulminant hepatitis, hepatic cirrhosis, pulmonary fibrosis, multiple sclerosis, systemic lupus erythematosus and rheumatoid arthritis.

2. The method according to claim 1, wherein the composition is administered by an administration method selected from the group consisting of intravenous administration, intra-arterial administration, intraportal administration, intracutaneous administration, subcutaneous administration, intramuscular administration, intraperitoneal administration and intranasal administration.

3. The method according to claim 1, wherein the inflammatory disease is selected from the group consisting of multiple sclerosis, systemic lupus erythematosus and rheumatoid arthritis.

4. The method according to claim 1, wherein the dental pulp cells are human dental pulp cells.

5. The method according to claim 1, wherein the inflammatory disease is selected from the group consisting of fulminant hepatitis, hepatic cirrhosis, and pulmonary fibrosis.

6. The method according to claim 1, wherein the inflammatory disease is hepatic cirrhosis.

* * * * *

UNITED STATES PATENT AND TRADEMARK OFFICE
CERTIFICATE OF CORRECTION

PATENT NO. : 10,709,741 B2
APPLICATION NO. : 14/767331
DATED : July 14, 2020
INVENTOR(S) : Akihito Yamamoto et al.

It is certified that error appears in the above-identified patent and that said Letters Patent is hereby corrected as shown below:

On the Title Page

Item (73), change:
"NATIONAL UNIVERSITY CORPORATION NAGOYA UNIVERSITY, Nagoya (JP)"

To:
--TOKUSHIMA UNIVERSITY, Tokushima (JP)--

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*